(12) United States Patent
Shudo

(10) Patent No.: US 12,138,082 B2
(45) Date of Patent: Nov. 12, 2024

(54) EVALUATION DEVICE, EVALUATION METHOD, AND NON-TRANSITORY STORAGE MEDIUM

(71) Applicant: JVCKENWOOD Corporation, Yokohama (JP)

(72) Inventor: Katsuyuki Shudo, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 719 days.

(21) Appl. No.: 17/347,628

(22) Filed: Jun. 15, 2021

(65) Prior Publication Data

US 2021/0298689 A1 Sep. 30, 2021

Related U.S. Application Data

(63) Continuation of application No. PCT/JP2019/036425, filed on Sep. 17, 2019.

(30) Foreign Application Priority Data

Dec. 28, 2018 (JP) ................. 2018-248423

(51) Int. Cl.
 *A61B 5/00* (2006.01)
 *A61B 5/16* (2006.01)
(52) U.S. Cl.
 CPC .............. *A61B 5/742* (2013.01); *A61B 5/163* (2017.08); *A61B 5/168* (2013.01)
(58) Field of Classification Search
 CPC ........... A61B 5/742; A61B 5/163; A61B 5/72; A61B 5/7271; A61B 5/16; A61B 5/74;
 (Continued)

(56) References Cited

U.S. PATENT DOCUMENTS

2020/0383626 A1* 12/2020 Takeda .................. A61B 5/163

FOREIGN PATENT DOCUMENTS

| JP | 2011-083403 | 4/2018 |
| JP | 2018-140007 | 9/2018 |

(Continued)

OTHER PUBLICATIONS

International Search Report and Written Opinion for International Application No. PCT/JP2019/036425 mailed on Dec. 3, 2019, 10 pages.

(Continued)

*Primary Examiner* — Travis S Fissel
(74) *Attorney, Agent, or Firm* — Amin, Turocy & Watson, LLP

(57) ABSTRACT

An evaluation device includes a display for images; a gaze point detecting unit configured to detect a positional data of a gaze point of a subject; a display controller configured to display, on the display, a task target object and instruction information, and then a specific target object including a specific feature portion as a correct answer to the instruction information and comparison target objects; an area setting unit configured to set a specific feature area for the specific feature portion and comparison areas for the comparison target objects on the display; a determination unit configured to determine, based on the detected positional data, whether the gaze point is present in the set areas; an arithmetic unit configured to calculate, based on a determination result, a gaze point transition data; and an evaluating unit configured to obtain, based on the gaze point transition data, an evaluation data.

5 Claims, 15 Drawing Sheets

(58) Field of Classification Search
CPC ..... A61B 5/743; A61B 3/0033; A61B 3/0041; A61B 3/0032; A61B 3/152; A61B 3/113; G16H 10/20; G16H 30/20; G16H 30/40; G16H 40/40; G16H 40/63; H04N 13/366; H04N 13/383
USPC .......................... 351/209–211, 205–206, 246
See application file for complete search history.

(56) References Cited

FOREIGN PATENT DOCUMENTS

| | | |
|---|---|---|
| WO | 2018/216347 | 11/2018 |
| WO | 2019/098173 | 5/2019 |

OTHER PUBLICATIONS

Extended European Search Report for European Patent Application No. 19905105.3 mailed Dec. 13, 2021.

\* cited by examiner

EVALUATION DEVICE, EVALUATION METHOD, AND NON-TRANSITORY STORAGE MEDIUM

CROSS-REFERENCE TO RELATED APPLICATIONS

This application is a Continuation of PCT International Application No. PCT/JP2019/036425 filed on Sep. 17, 2019 which claims the benefit of priority from Japanese Patent Application No. 2018-248423 filed on Dec. 28, 2018, the entire contents of which are incorporated herein by reference.

FIELD

The present application relates to an evaluation device, an evaluation method, and an evaluation program.

BACKGROUND

In recent years, it is said that cognitive functional impairment and brain functional impairment are increasing, and a demand for detecting cognitive functional impairment and brain functional impairment early and a demand for quantitatively evaluating severity of symptoms are required. It is known that symptoms of cognitive functional impairment and brain functional impairment affect cognitive ability. Therefore, an evaluation is performed on a subject based on cognitive ability of the subject. For example, an apparatus that displays multiple numbers, instructs a subject to add the numbers to obtain an answer, and checks the answer provided by the subject has been proposed (for example, see Japanese Laid-open Patent Publication No. 2011-083403).

SUMMARY

However, in the method described in Patent Literature 1 or the like, the subject selects an answer by operating a touch panel or the like and it is thus difficult to obtain high evaluation accuracy due to a correct answer by chance or an error in operation performed by the subject.

Therefore, there have been demands for evaluating cognitive functional impairment and brain functional impairment with high accuracy.

An evaluation device, an evaluation method, and a non-transitory storage medium are disclosed.

According to one aspect, there is provided an evaluation device comprising: a display configured to display images; a gaze point detecting unit configured to detect a positional data of a gaze point of a subject who observes the display; a display controller configured to display a task target object that includes a task feature portion and that is to be gazed at by the subject and instruction information that is a task related to the task target object on the display, and to display, after displaying the task target object and the instruction information, a specific target object that includes a specific feature portion corresponding to the task feature portion and that is a correct answer to the instruction information and comparison target objects each of which differs from the specific target object on the display; an area setting unit configured to set a specific feature area for the specific feature portion and comparison areas for the comparison target objects on the display; a determination unit configured to determine, based on the positional data of the gaze point, whether the gaze point is present in each of the specific feature area and the comparison areas; an arithmetic unit configured to calculate, based on a determination result by the determination unit, a gaze point transition data in a target display period; and an evaluating unit configured to obtain, based on the gaze point transition data in the target display period, an evaluation data of the subject.

According to one aspect, there is provided an evaluation method comprising: displaying images on a display; detecting a positional data of a gaze point of a subject who observes the display; displaying a task target object that includes a task feature portion and that is to be gazed at by the subject and instruction information that is a task related to the task target object on the display, and displaying, after displaying the task target object and the instruction information, a specific target object that includes a specific feature portion corresponding to the task feature portion and that is a correct answer to the instruction information and comparison target objects each of which differs from the specific target object on the display; setting a specific feature area for the specific feature portion and comparison areas for the comparison target objects on the display; determining, based on the positional data of the gaze point, whether the gaze point is present in each of the specific feature area and the comparison areas; calculating, based on a determination result, a gaze point transition data in a target display period; and obtaining, based on the gaze point transition data in the target display period, an evaluation data of the subject.

According to one aspect, there is provided a non-transitory storage medium that stores an evaluation program that causes a computer to execute: a process of displaying images on a display; a process of detecting a positional data of a gaze point of a subject who observes the display; a process of displaying a task target object that includes a task feature portion and that is to be gazed at by the subject and instruction information that is a task related to the task target object on the display, and displaying, after displaying the task target object and the instruction information, a specific target object that includes a specific feature portion corresponding to the task feature portion and that is a correct answer to the instruction information and comparison target objects each of which differs from the specific target object on the display; a process of setting a specific feature area for the specific feature portion and comparison areas for the comparison target objects on the display; a process of determining, based on the positional data of the gaze point, whether the gaze point is present in each of the specific feature area and the comparison areas; a process of calculating, based on a determination result, a gaze point transition data in a target display period; and a process of obtaining, based on the gaze point transition data in the target display period, an evaluation data of the subject.

The above and other objects, features, advantages and technical and industrial significance of this application will be better understood by reading the following detailed description of presently preferred embodiments of the application, when considered in connection with the accompanying drawings.

DETAILED DESCRIPTION OF THE PREFERRED EMBODIMENTS

Preferred embodiments of an evaluation device, an evaluation method, and an evaluation program according to the present disclosure will be described based on the drawings. Furthermore, the present application is not limited to the embodiments. Furthermore, the components described in the embodiments include one that can easily be replaced by those skilled in the art or one that is substantially identical.

In a description below, the positional relationships among components will be described by setting a three-dimensional global coordinate system. It is assumed that a direction parallel to a first axis of a predetermined plane is defined as an X-axis direction, a direction parallel to a second axis of the predetermined plane orthogonal to the first axis is defined as a Y-axis direction, and a direction parallel to a third axis that is orthogonal to each of the first axis and the second axis is defined as a Z-axis direction. The predetermined plane includes an XY plane.

Line-of-Sight Detecting Device

Figure 1:
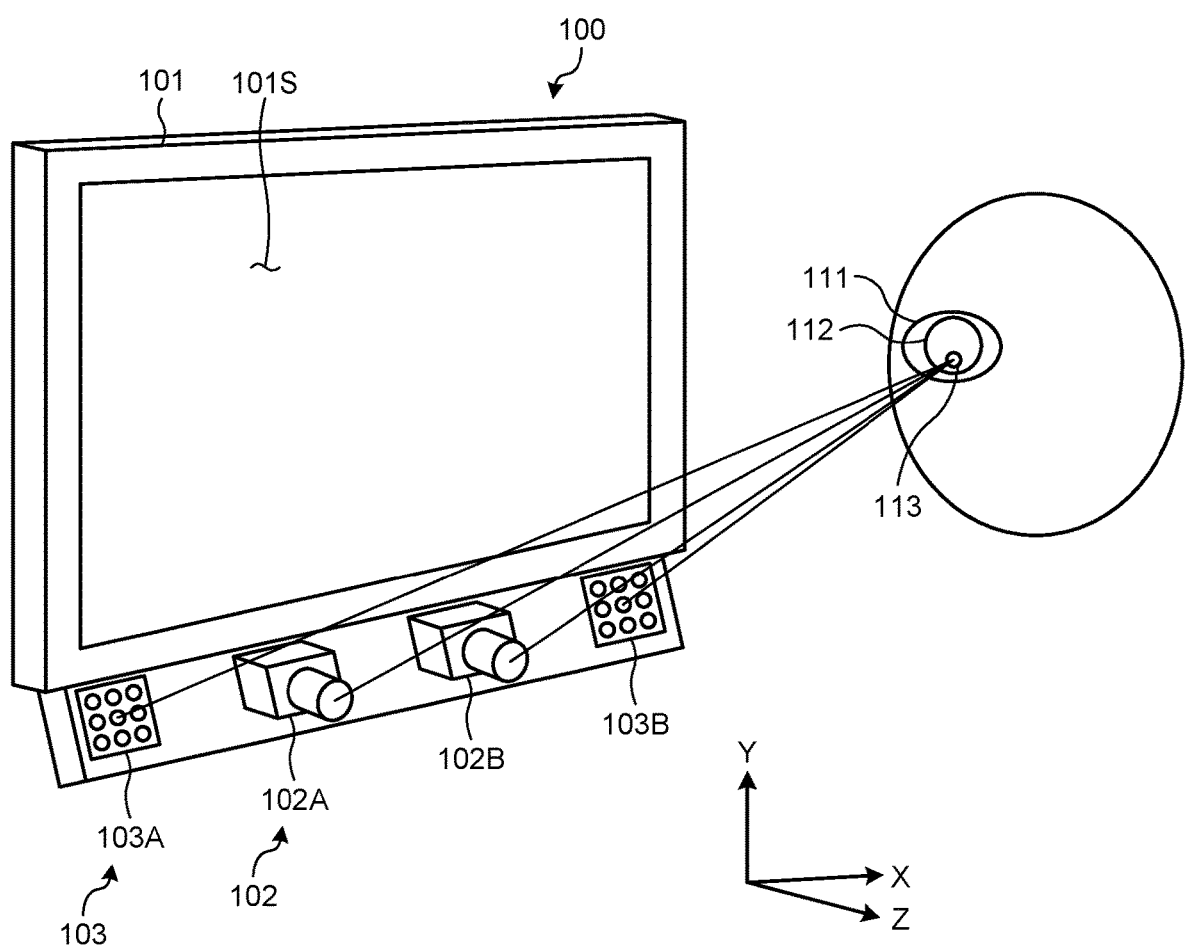
FIG. 1 is a perspective view schematically illustrating an example of a line-of-sight detecting device according to one embodiment.

FIG. 1 is a perspective view schematically illustrating an example of a line-of-sight detecting device 100 according to a first embodiment. The line-of-sight detecting device 100 is used as an evaluation device that evaluates cognitive functional impairment and brain functional impairment. As illustrated in FIG. 1, the line-of-sight detecting device 100 includes a display device 101, a stereo camera device 102, and an illuminating device 103.

The display device 101 includes a flat panel display, such as a liquid crystal display (LCD) or an organic electroluminescence (EL) display (OLED). In the embodiment, the display device 101 includes a display 101S. The display 101S displays an image. In the embodiment, the display 101S displays an index for evaluating, for example, a visual performance of a subject. The display 101S is substantially parallel to the XY plane. The X-axis direction corresponds to the horizontal direction of the display 101S, the Y-axis direction corresponds to the vertical direction of the display 101S, and the Z-axis direction corresponds to the depth direction orthogonal to the display 101S.

The stereo camera device 102 includes a first camera 102A and a second camera 102B. The stereo camera device 102 is arranged below the display 101S of the display device 101. The first camera 102A and the second camera 102B are arranged in the X-axis direction. The first camera 102A is arranged in the negative X direction relative to the second camera 102B. Each of the first camera 102A and the second camera 102B includes an infrared camera and includes, an optical system capable of transmitting near-infrared light with a wavelength of, for example, 850 (nm) and an image sensor capable of receiving the near-infrared light.

The illuminating device 103 includes a first light source 103A and a second light source 103B. The illuminating device 103 is arranged below the display 101S of the display device 101. The first light source 103A and the second light source 103B are arranged in the X-axis direction. The first light source 103A is arranged in the negative direction relative to the first camera 102A. The second light source 103B is arranged in the positive direction relative to the second camera 102B. Each of the first light source 103A and the second light source 103B includes a light emitting diode (LED) light source and is able to emit near-infrared light with a wavelength of, for example, 850 (nm). Furthermore, the first light source 103A and the second light source 103B may also be arranged between the first camera 102A and the second camera 102B.

The illuminating device 103 emits near-infrared light that is detection light and illuminates an eyeball 111 of a subject. The stereo camera device 102 captures an image of a part of the eyeball 111 (hereinafter, referred to as an "eyeball" including the part of the eyeball) by the second camera 102B when the eyeball 111 is irradiated with the detection light emitted from the first light source 103A and captures an image of the eyeball 111 by the first camera 102A when the eyeball 111 is irradiated with the detection light emitted from the second light source 103B.

A frame synchronization signal is output from at least one of the first camera 102A and the second camera 102B. The first light source 103A and the second light source 103B output detection light based on the frame synchronization signal. The first camera 102A captures image data of the eyeball 111 when the eyeball 111 is irradiated with the detection light emitted from the second light source 103B.

The second camera 102B captures image data of the eyeball 111 when the eyeball 111 is irradiated with the detection light emitted from the first light source 103A.

When the eyeball 111 is irradiated with the detection light, a part of the detection light is reflected at a pupil 112 and the light from the pupil 112 is incident into the stereo camera device 102. Furthermore, when the eyeball 111 is irradiated with the detection light, a corneal reflection image 113 that is a virtual image of a cornea is formed on the eyeball 111 and the light from the corneal reflection image 113 is incident into the stereo camera device 102.

By appropriately setting the relative position between a set of the first camera 102A and the second camera 102B and a set of the first light source 103A and the second light source 103B, the intensity of the light incident from the pupil 112 to the stereo camera device 102 is reduced and the intensity of the light incident from the corneal reflection image 113 to the stereo camera device 102 is increased. That is, the image of the pupil 112 captured by the stereo camera device 102 has a low luminance and the image of the corneal reflection image 113 has a high luminance. The stereo camera device 102 can detect the position of the pupil 112 and a position of the corneal reflection image 113 based on the luminance of the image captured.

Figure 2:
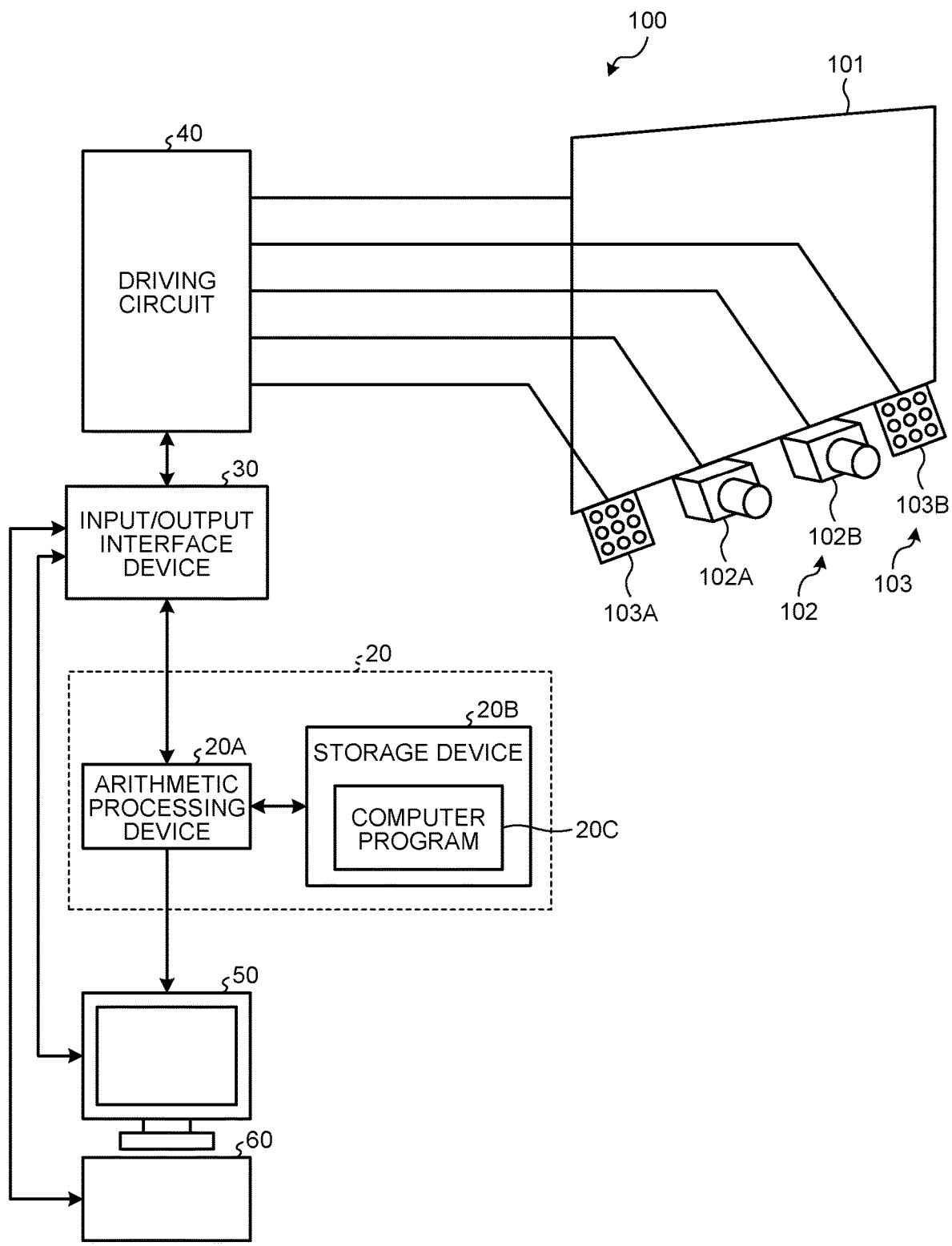
FIG. 2 is a diagram illustrating an example of a hardware configuration of the line-of-sight detecting device according to the embodiment.

FIG. 2 is a diagram illustrating an example of a hardware configuration of the line-of-sight detecting device 100 according to the embodiment. As illustrated in FIG. 2, the line-of-sight detecting device 100 includes the display device 101, the stereo camera device 102, the illuminating device 103, a computer system 20, an input/output interface device 30, a driving circuit 40, an output device 50, and an input device 60.

The computer system 20, the driving circuit 40, the output device 50, and the input device 60 perform data communication via the input/output interface device 30. The computer system 20 includes an arithmetic processing device 20A and a storage device 20B. The arithmetic processing device 20A includes a microprocessor, such as a central processing unit (CPU). The storage device 20B includes a memory, such as a read only memory (ROM) and a random access memory (RAM), or storage. The arithmetic processing device 20A performs arithmetic processing in accordance with a computer program 20C that is stored in the storage device 20B.

The driving circuit 40 generates a driving signal and outputs the driving signal to the display device 101, the stereo camera device 102, and the illuminating device 103. Furthermore, the driving circuit 40 supplies the image data of the eyeball 111 captured by the stereo camera device 102 to the computer system 20 via the input/output interface device 30.

The output device 50 includes a display, such as a flat panel display. Furthermore, the output device 50 may also include a printer. The input device 60 generates input data by being operated. The input device 60 includes a keyboard or a mouse for a computer system. Furthermore, the input device 60 may also include a touch sensor arranged on the display of the output device 50 as a display.

In the embodiment, the display device 101 and the computer system 20 are separated devices. Furthermore, the display device 101 and the computer system 20 may also be integrated. For example, if the line-of-sight detecting device 100 includes a tablet type personal computer, the computer system 20, the input/output interface device 30, the driving circuit 40, and the display device 101 may also be mounted on the tablet type personal computer.

Figure 3:
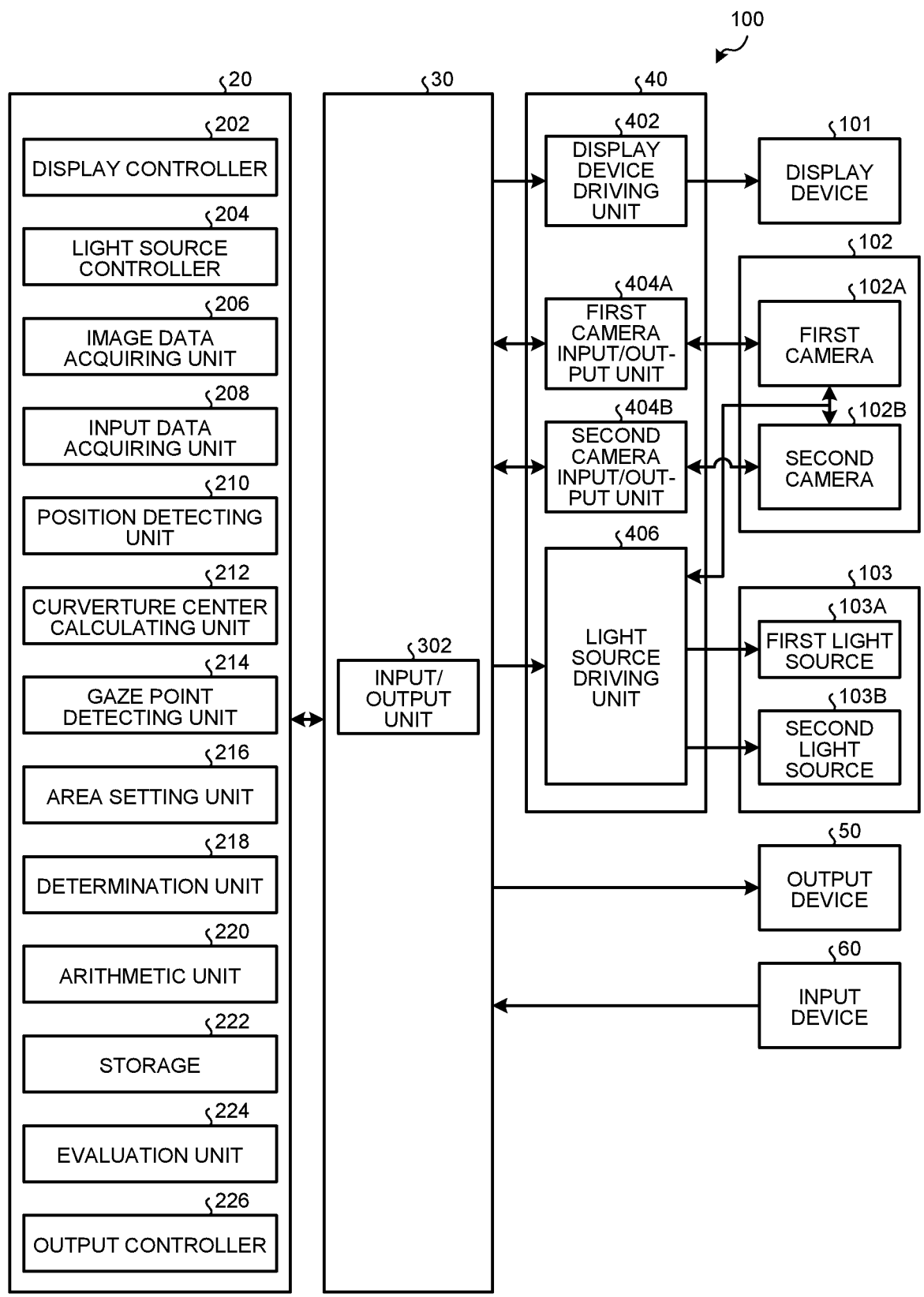
FIG. 3 is a functional block diagram illustrating an example of the line-of-sight detecting device according to the embodiment.

FIG. 3 is a functional block diagram illustrating an example of the line-of-sight detecting device 100 according to the embodiment. As illustrated in FIG. 3, the input/output interface device 30 includes an input/output unit 302. The driving circuit 40 includes a display device driving unit 402 that generates a driving signal for driving the display device 101 and that outputs the driving signal to the display device 101; a first camera input/output unit 404A that generates a driving signal for driving the first camera 102A and that outputs the driving signal to the first camera 102A; a second camera input/output unit 404B that generates a driving signal for driving the second camera 102B and that outputs the driving signal to the second camera 102B; and a light source driving unit 406 that generates a driving signal for driving the first light source 103A and the second light source 103B and that outputs the driving signal to the first light source 103A and the second light source 103B. Furthermore, the first camera input/output unit 404A supplies the image data of the eyeball 111 captured by the first camera 102A to the computer system 20 via the input/output unit 302. The second camera input/output unit 404B supplies the image data of the eyeball 111 captured by the second camera 102B to the computer system 20 via the input/output unit 302.

The computer system 20 controls the line-of-sight detecting device 100. The computer system 20 includes a display controller 202, a light source controller 204, an image data acquiring unit 206, an input data acquiring unit 208, a position detecting unit 210, a curvature center calculating unit 212, a gaze point detecting unit 214, an area setting unit 216, a determination unit 218, an arithmetic unit 220, a storage 222, an evaluation unit 224, and an output controller 226. The function of the computer system 20 is performed by the arithmetic processing device 20A and the storage device 20B.

The display controller 202 performs an instruction display operation of displaying, on the display 101S, a task target object that is to be gazed at by the subject and instruction information that is a task related to the task target object. The task target object includes a task feature portion. The task feature portion is a portion that can be an appearance feature when the subject memorizes the task feature portion. For example, a recess portion or a protruding portion of a pattern that constitutes the task target object or a connection portion or the like of multiple patterns can be used as the task feature portion. Examples of the connection portion of the multiple patterns include an overlapping portion, a contact portion, an intersection portion, and the like of the multiple patterns. The instruction information includes characters, a figure, and the like that are able to be displayed on the display 101S. An example of the task includes a task that allows the subject to memorize the task target object and select the same target object as the memorized task target object.

Furthermore, after the instruction display operation, the display controller 202 performs a target display operation of displaying, on the display 101S, a specific target object that is a correct answer to the instruction information and comparison target objects each of which differs from the specific target object. The specific target object includes a specific feature portion that is associated with the task feature portion. Similarly to the task feature portion, a recess portion or a protruding portion of the pattern that constitutes the specific target object or a connection portion or the like of multiple patterns can be used as the specific feature portion. Examples of the connection portion of the multiple patterns include an overlapping portion, a contact portion, and an intersection portion. Furthermore, for example, if a task that allows the subject to select the same target object as the memorized task target object is given as described above, the specific target object corresponds to the same target object as the task target object in appearance. Therefore, in this case, the specific feature portion is the same portion as the task feature portion.

The task target object, the instruction information, the specific target object, and the comparison target objects are included in, for example, an evaluation purpose video or an evaluation purpose image that is to be visually confirmed by the subject. The display controller 202 displays the evaluation purpose video or the evaluation purpose image on the display 101S. Furthermore, the instruction information is not limited to a mode that uses, for example, a sentence using characters. The instruction information may also be a mode that uses, for example, a combination of figures without using characters as long as the instruction information is able to convey the task to the subject.

The light source controller 204 controls the light source driving unit 406 and controls an operation state of the first light source 103A and the second light source 103B. The light source controller 204 controls the first light source 103A and the second light source 103B such that the first light source 103A and the second light source 103B emit the detection light at different timings.

The image data acquiring unit 206 acquires, from the stereo camera device 102 via the input/output unit 302, the image data of the eyeball 111 of the subject captured by the stereo camera device 102 that includes the first camera 102A and the second camera 102B.

The input data acquiring unit 208 acquires, from the input device 60 via the input/output unit 302, the input data generated by an operation of the input device 60.

The position detecting unit 210 detects positional data of the pupil center based on the image data of the eyeball 111 acquired by the image data acquiring unit 206. Furthermore, the position detecting unit 210 detects positional data of the corneal reflection center based on the image data of the eyeball 111 acquired by the image data acquiring unit 206. The pupil center is a center of the pupil 112. The corneal reflection center is a center of the corneal reflection image 113. The position detecting unit 210 detects, for each of the left and right eyeballs 111 of the subject, the positional data of the pupil center and the positional data of the corneal reflection center.

The curvature center calculating unit 212 calculates positional data of a corneal curvature center of the eyeball 111 based on the image data of the eyeball 111 acquired by the image data acquiring unit 206.

The gaze point detecting unit 214 detects positional data of the gaze point P of the subject based on the image data of the eyeball 111 acquired by the image data acquiring unit 206. In the present embodiment, the positional data of the gaze point P indicates the positional data of an intersection point between a line-of-sight vector of the subject that is defined by the three-dimensional global coordinate system and the display 101S of the display device 101. The gaze point detecting unit 214 detects a line-of-sight vector of each of the right and left eyeballs 111 of the subject based on the positional data of the pupil center and the positional data of the corneal curvature center that are acquired from the image data of the eyeball 111. After the line-of-sight vector has been detected, the gaze point detecting unit 214 detects the positional data of the gaze point P indicating the intersection point between the line-of-sight vector and the display 101S.

The area setting unit 216 sets, on the display 101S, in an instruction display period for which the instruction display operation is being performed, a task feature area for the task feature portion of the task target object and an instruction area for the instruction information. Furthermore, the area setting unit 216 sets, on the display 101S, in the target display period for which the target display operation is being performed, a specific feature area for the specific feature portion of the specific target object and comparison areas for the comparison target objects.

The determination unit 218 determines, in the instruction display period, based on the positional data of the gaze point P, whether the gaze point P is present in each of the task feature area and the instruction area, and then, outputs determination data. The determination unit 218 determines whether the gaze point P is present in each of the task feature area and the instruction area at, for example, regular intervals. Furthermore, the determination unit 218 determines, in the target display period, based on the positional data of the gaze point P, whether the gaze point P is present in each of the specific feature area and the comparison areas, and then, outputs determination data. The determination unit 218 determines whether the gaze point P is present in each of the specific area and the comparison areas at, for example, regular intervals. The regular interval is, for example, a period (for example, every 20 (msec)) of a frame synchronization signal that is output from each of the first camera 102A and the second camera 102B.

The arithmetic unit 220 calculates, based on the determination data by the determination unit 218, a gaze point transition data in the instruction display period that indicates a transition of the gaze point P in the instruction display period. Furthermore, the arithmetic unit 220 calculates, based on the determination data by the determination unit 218, a gaze point transition data in the target display period that indicates a transition of the gaze point P in the target display period.

The gaze point transition data in the instruction display period includes a first presence time data that indicates a presence time in which the gaze point P is present in the task feature area in the instruction display period, a second presence time data that indicates a presence time in which the gaze point P is present in the instruction area in the instruction display period, an arrival time data in the instruction display period that indicates a time period from a start time of the instruction display period to an arrival time at which the gaze point P arrives at the task feature area, and a moving frequency data in the instruction display period that indicates the number of times of position movement of the gaze point P between the task feature area and the instruction area.

The gaze point transition data in the target display period includes an arrival time data in the target display period that indicates a time period from a start time of the target display period to an arrival time at which the gaze point P arrives at the specific feature area, a moving frequency data in the target display period that indicates the number of times of position movement of the gaze point P between multiple comparison areas until the gaze point P first arrives at the specific feature area, a presence time data in the target display period that indicates a presence time in which the gaze point P is present in the specific feature area in the target display period, and a final area data that indicates an area in which the gaze point P is finally present among the specific feature area and the comparison areas in the target display period.

Furthermore, the arithmetic unit 220 includes a management timer that manages a playback time of a video and a detection timer T1 that detects an elapsed time from displaying the video on the display 101S. The arithmetic unit 220 includes a counter that counts the number of determination that the gaze point P is present in the specific area.

The evaluation unit 224 obtains evaluation data of the subject based on the gaze point transition data in the target display period. Furthermore, the evaluation unit 224 is able to obtain the evaluation data of the subject based on the gaze point transition data in the instruction display period and the gaze point transition data in the target display period. The evaluation data includes data that is used to evaluate, in the instruction display operation, whether the subject is able to gaze at the task target object and the instruction information that are displayed on the display 101S. Furthermore, the evaluation data includes data that is used to evaluate, in the target display operation, whether the subject is able to gaze at the specific target object and the comparison target objects that are displayed on the display 101S.

The storage 222 stores therein the determination data, the gaze point transition data in the instruction display period (the first presence time data, the second presence time data, the arrival time data in the instruction display period, and the movement frequency data in the instruction display period), the gaze point transition data in the target display period (the presence time data in the target display period, the movement frequency data in the target display period, the final area data, and the arrival time data in the target display period), and the evaluation data, which are described above. Furthermore, the storage 222 stores therein an evaluation program that causes a computer to execute a process of displaying an image on the display 101S; a process of detecting the positional data of the gaze point P of the subject who observes the display 101S; a process of displaying, after displaying the task target object that includes the task feature portion and that is to be gazed at by the subject and the instruction information that is a task for the task target object on the display 101S, the specific target object that includes the specific feature portion for the task feature portion and corresponds to a correct answer to the instruction information and the comparison target objects that differs from the specific target object on the display 101S; a process of setting, on the display 101S, the specific feature area for the specific feature portion and the comparison areas for the comparison target objects; a process of determining, based on the positional data of the gaze point P, whether the gaze point P is present in each of the specific feature area and the comparison areas; a process of calculating, based on the determination result, the gaze point transition data in the target display period; and a process of obtaining, based on the gaze point transition data in the target display period, evaluation data of the subject.

The output controller 226 outputs the data to at least one of the display device 101 and the output device 50.

Figure 4:
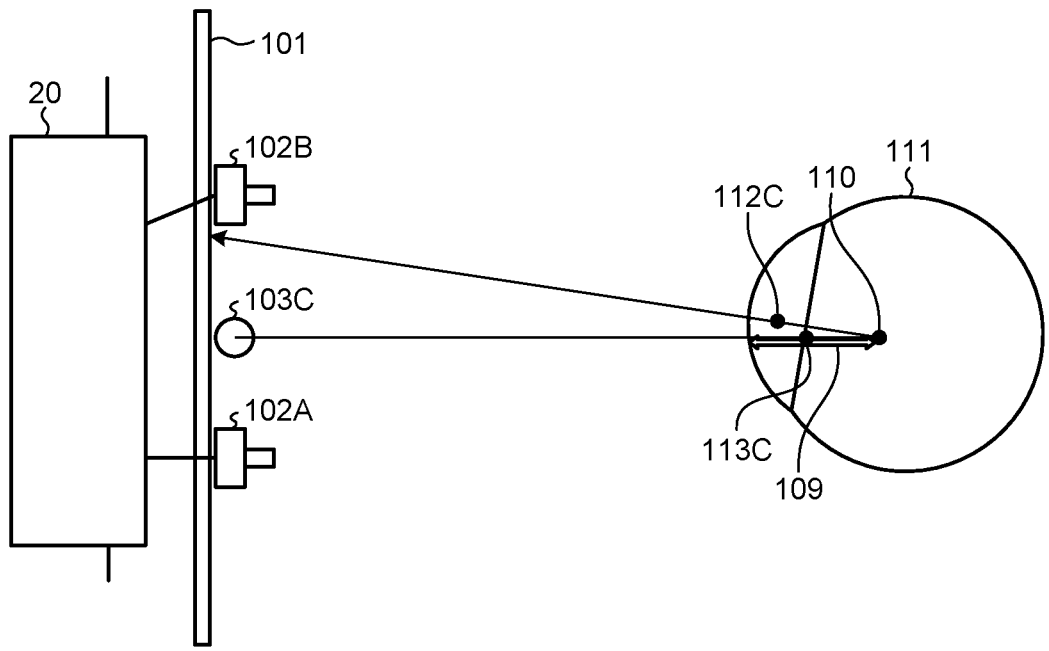
FIG. 4 is a schematic diagram illustrating a method for calculating a positional data of a corneal curvature center according to the embodiment.
Figure 5:
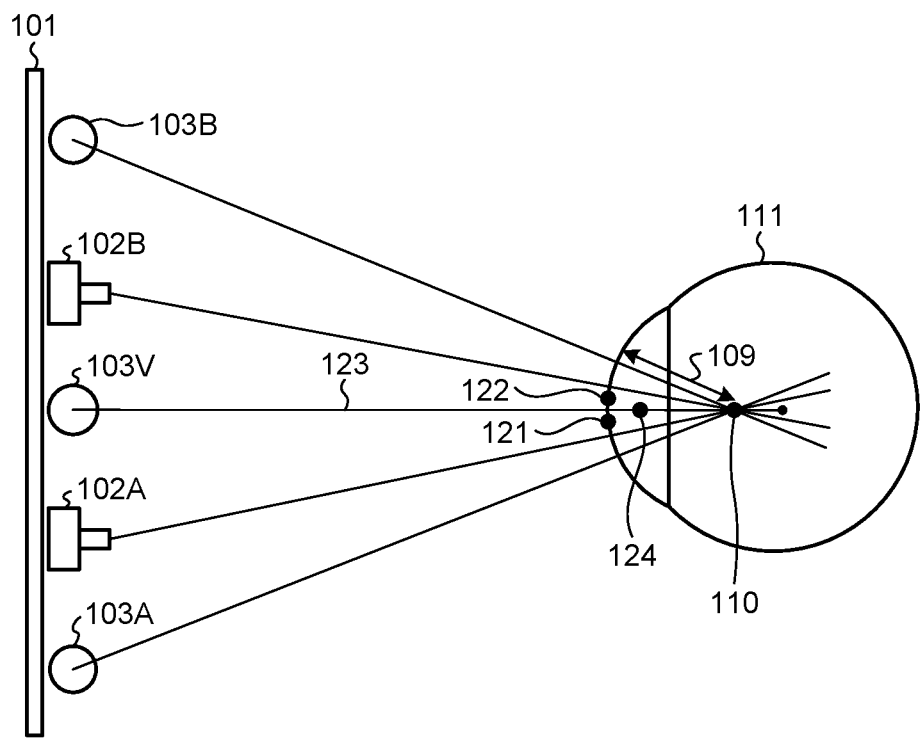
FIG. 5 is a schematic diagram illustrating a method for calculating a positional data of a corneal curvature center according to the embodiment.

In the following, an outline of processes performed by the curvature center calculating unit 212 according to the embodiment will be described. The curvature center calculating unit 212 calculates the positional data of the corneal curvature center of the eyeball 111 based on the image data of the eyeball 111. Each of FIG. 4 and FIG. 5 is a schematic diagram illustrating a calculation method of positional data of a corneal curvature center 110 according to the embodiment. FIG. 4 illustrates an example in which the eyeball 111 is illuminated by a light source 103C. FIG. 5 illustrates an example in which the eyeball 111 is illuminated by the first light source 103A and the second light source 103B.

First, the example illustrated in FIG. 4 will be described. The light source 103C is arranged between the first camera 102A and the second camera 102B. A pupil center 112C is a center of the pupil 112. A corneal reflection center 113C is a center of the corneal reflection image 113. In FIG. 4, the pupil center 112C indicates a pupil center when the eyeball 111 is illuminated by the single light source 103C. The corneal reflection center 113C indicates a corneal reflection center when the eyeball 111 is illuminated by the single light source 103C. The corneal reflection center 113C is present on a straight line connecting the light source 103C and a corneal curvature center 110. The corneal reflection center 113C is positioned at a middle point between a cornea surface and the corneal curvature center 110. A corneal curvature radius 109 is a distance between the cornea surface and the corneal curvature center 110. Positional data of the corneal reflection center 113C is detected by the stereo camera device 102. The corneal curvature center 110 is present on a straight line connecting the light source 103C and the corneal reflection center 113C. The curvature center calculating unit 212 calculates, as the positional data of the corneal curvature center 110, positional data of a position which is located at a predetermined distance from the corneal reflection center 113C on the straight line. The predetermined value is a value that is determined in advance from a curvature radius value of a general cornea or the like and is stored in the storage 222.

In the following, the example illustrated in FIG. 5 will be described. In the embodiment, a set of the first camera 102A and the second light source 103B and a set of the second camera 102B and the first light source 103A are arranged at bilaterally symmetrical positions with respect to a straight line that passes through an intermediate position between the first camera 102A and the second camera 102B. It is assumed that a virtual light source 103V is present at the intermediate position between the first camera 102A and the second camera 102B. A corneal reflection center 121 indicates a corneal reflection center in an image that is obtained by capturing the eyeball 111 by the second camera 102B. A corneal reflection center 122 indicates a corneal reflection center in an image that is obtained by capturing the eyeball 111 by the first camera 102A. A corneal reflection center 124 indicates a corneal reflection center associated with the virtual light source 103V. Positional data of the corneal reflection center 124 is calculated based on positional data of the corneal reflection center 121 and positional data of the corneal reflection center 122 that are captured by the stereo camera device 102. The stereo camera device 102 detects the positional data of the corneal reflection center 121 and the positional data of the corneal reflection center 122 in the three-dimensional local coordinate system that is defined in the stereo camera device 102. A camera calibration using a stereo calibration method is performed in advance on the stereo camera device 102, and a transformation parameter for transforming the three dimensional local coordinate system of the stereo camera device 102 into the three-dimensional global coordinate system is calculated. The transformation parameter is stored in the storage 222. The curvature center calculating unit 212 transforms the positional data of the corneal reflection center 121 and the positional data of the corneal reflection center 122 captured by the stereo camera device 102 into the positional data in the three-dimensional global coordinate system by using the transformation parameter. The curvature center calculating unit 212 calculates the positional data of the corneal reflection center 124 in the three-dimensional global coordinate system based on the positional data of the corneal reflection center 121 and the positional data of the corneal reflection center 122 that are defined in the three-dimensional global coordinate system. The corneal curvature center 110 is present on a straight line 123 connecting the virtual light source 103V and the corneal reflection center 124. The curvature center calculating unit 212 calculates, as the positional data of the corneal curvature center 110, positional data of a position which is located at a predetermined distance from the corneal reflection center 124 on the straight line 123. The predetermined value is a value that is determined in advance from a curvature radius value of a general cornea or the like and is stored in the storage 222.

In this way, even when two light sources are present, the corneal curvature center 110 is calculated by the same method as the method that is used when a single light source is present.

The corneal curvature radius 109 corresponds to a distance between the cornea surface and the corneal curvature center 110. Accordingly, the corneal curvature radius 109 is calculated by calculating the positional data of the cornea surface and the positional data of the corneal curvature center 110.

Figure 6:
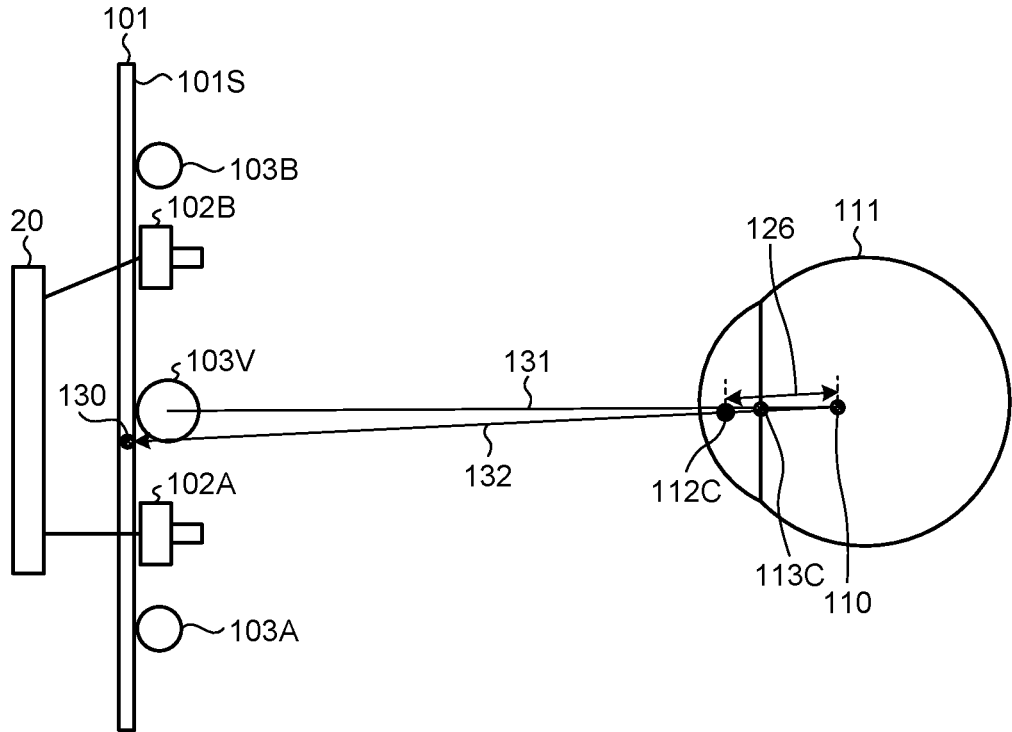
FIG. 6 is a schematic diagram illustrating an example of a calibration process according to the embodiment.

In the following, an example of a line-of-sight detecting method according to the embodiment will be described. FIG. 6 is a schematic diagram illustrating an example of a calibration process according to the embodiment. In the calibration process, a target position 130 is set in order to allow the subject to gaze steadily. The target position 130 is defined in the three-dimensional global coordinate system. In the embodiment, the target position 130 is set at, for example, a middle position of the display 101S of the display device 101. Furthermore, the target position 130 may also be set at an edge position of the display 101S. The output controller 226 displays a target image at the set target position 130. A straight line 131 is a straight line connecting the virtual light source 103V and the corneal reflection center 113C. A straight line 132 is a straight line connecting the target position 130 and the pupil center 112C. The corneal curvature center 110 is an intersection point between the straight line 131 and the straight line 132. The curvature center calculating unit 212 can calculate the positional data of the corneal curvature center 110 based on the positional data of the virtual light source 103V, the positional data of the target position 130, the positional data of the pupil center 112C, and the positional data of the corneal reflection center 113C.

Figure 7:
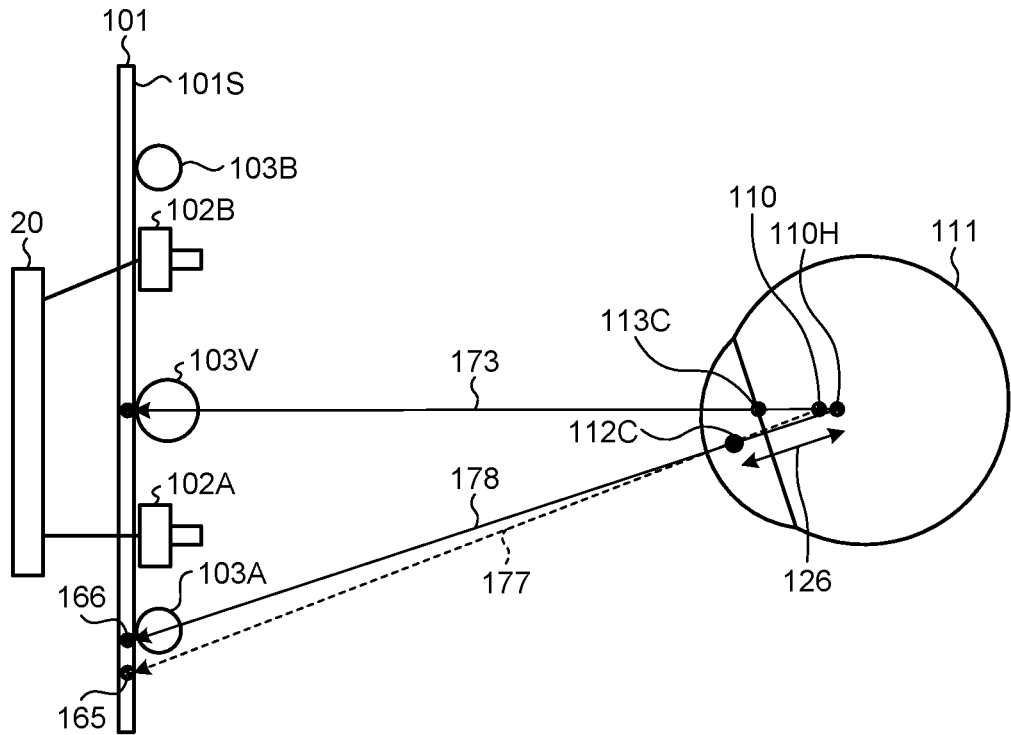
FIG. 7 is a schematic diagram illustrating an example of a gaze point detecting process according to the embodiment.

In the following, a gaze point detecting process performed by the gaze point detecting unit 214 will be described. The gaze point detecting process is performed after the calibration process. The gaze point detecting unit 214 calculates a line-of-sight vector of the subject and positional data of the gaze point P based on the image data of the eyeball 111. FIG. 7 is a schematic diagram illustrating an example of the gaze point detecting process according to the embodiment. In FIG. 7, a gaze point 165 indicates a gaze point P that is obtained from the corneal curvature center calculated using a general curvature radius value. A gaze point 166 indicates a gaze point P that is obtained from the corneal curvature center calculated using a distance 126 obtained in the calibration process. The pupil center 112C indicates the pupil center calculated in the calibration process, and the corneal reflection center 113C indicates the corneal reflection center calculated in the calibration process. A straight line 173 is a straight line connecting the virtual light source 103V and the corneal reflection center 113C. The corneal curvature center 110 corresponds to a position of the corneal curvature center that is calculated from a general curvature radius value. The distance 126 is a distance between the pupil center 112C and the corneal curvature center 110 calculated in the calibration process. A corneal curvature center 110H indicates a corrected position of the corneal curvature center that has been corrected by using the distance 126. The corneal curvature center 110H is obtained under a condition that the corneal curvature center 110 is present on the straight line 173 and the distance between the pupil center 112C and the corneal curvature center 110 is the distance 126. Accordingly, a line of sight 177 that is calculated in a case of using the general curvature radius value is corrected to a line of sight 178. Furthermore, the gaze point P on the display 101S of the display device 101 is corrected from the gaze point 165 to the gaze point 166.

Evaluation Method

In the following, the evaluation method according to the embodiment will be described. In the evaluation method according to the embodiment, a developmental disability is evaluated as a visual performance of the subject by using the line-of-sight detecting device 100 described above.

Figure 8:
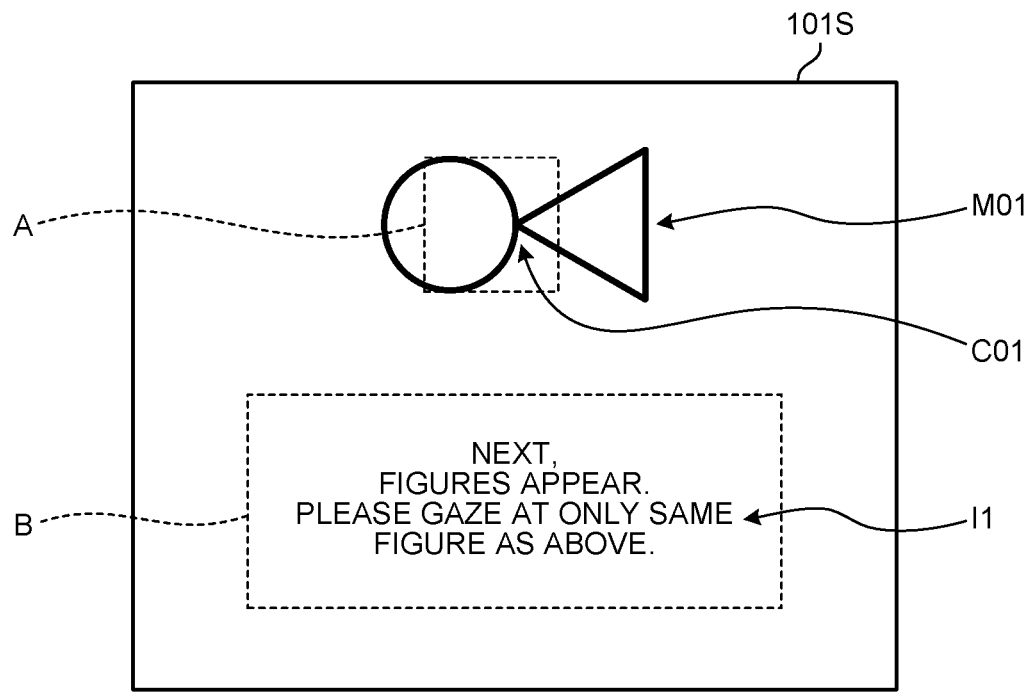
FIG. 8 is a diagram illustrating an example of content that is displayed on a display in an instruction display operation.

FIG. 8 is a diagram illustrating an example of content that is displayed on the display 101S in the instruction display operation. As illustrated in FIG. 8, the display controller 202 displays, on the display 101S in the instruction display operation, a task target object M01 that is to be gazed at by the subject and instruction information I1 that instructs the subject to accomplish a task for the task target object M01. In this case, a task with content that instructs to memorize a figure of the task target object M01 and select the same target object as the memorized task target object M01 is indicated as an example. In this case, the display controller 202 is able to display, on the display 101S, the task target object M01 and the instruction information I1 so as not to overlap with each other. In the example illustrated in FIG. 8, the task target object M01 has a shape of a combination of multiple patterns. Specifically, the task target object M01 has a shape of a combination of a circle and an equilateral triangle and one of the vertices of the equilateral triangle is brought into contact with a circumference of the circle. In the task target object M01, the contact portion in which the one of the vertices of the equilateral triangle is brought into contact with the circumference of the circle is a portion that can be an appearance feature when the subject memorizes the task target object M01, i.e., a task feature portion C01.

In the instruction display period for which the instruction display operation is being performed, the area setting unit 216 sets a task feature area A in a rectangular region that includes, for example, the task feature portion C01 of the task target object M01. The task feature area A does not need to include an entirety of the task target object M1 as long as the task feature area A includes a part of the task feature portion C01.

Furthermore, the area setting unit 216 sets an instruction area B in a rectangular region that includes, for example, the instruction information I1. The area setting unit 216 sets the task feature area A and the instruction area B on the display 101S at positions such that these areas do not overlap with each other. Furthermore, the shape of each of the task feature area A and the instruction area B is not limited to a rectangle, and the shape thereof may also be another shape, such as a circular shape, an elliptical shape, or a polygonal shape.

Figure 9:
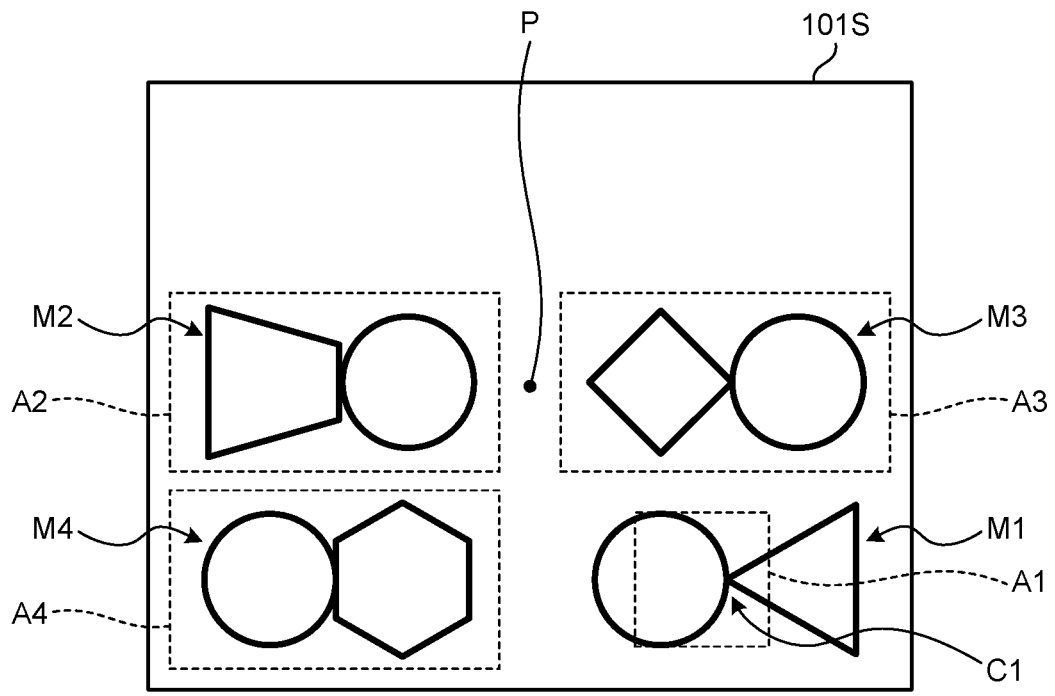
FIG. 9 is a diagram illustrating an example of a case in which multiple target objects are displayed on the display in a target display operation.

FIG. 9 is a diagram illustrating an example of a case in which multiple target objects are displayed on the display 101S in the target display operation. After the display controller 202 performs the instruction display operation in a predetermined period of time, the display controller 202 displays, on the display 101S as the target display operation, as illustrated in FIG. 9, a specific target object M1 that is a correct answer to the instruction information I1 and multiple comparison target objects M2 to M4 that are incorrect answers to the instruction information I1.

Here, when based on the content of the instruction information I1, the task target object M01 and the specific target object M1 are the same target object in appearance. Therefore, similarly to the task target object M01, the specific target object M1 has a shape of a combination of a circle and an equilateral triangle and one of the vertices of the equilateral triangle is brought into contact with the circumference of the circle. The comparison target objects M2 to M4 may also have the shape that is similar to the shape of the specific target object M1 or may also have the shape that is not similar to the shape of the specific target object M1. In the example illustrated in FIG. 9, the comparison target object M2 has a shape of a combination of a trapezoid and a circle, the comparison target object M3 has a shape of a combination of a square and a circle, and the comparison target object M4 has a shape of a combination of a circle and a regular hexagon. The display controller 202 displays, on the display 101S, the multiple target objects including the specific target object M1 and the comparison target objects M2 to M4, thereby allowing the subject to find the specific target object M1 and gaze at the found specific target object M1.

Furthermore, FIG. 9 illustrates an example of a gaze point P that is displayed on the display 101S as a result of a measurement. However, in practice, the gaze point P is not displayed on the display 101S. Detection of the positional data of the gaze point P is performed in, for example, a period (for example, every 20 (msec)) of a frame synchronization signal that is output from the first camera 102A and the second camera 102B. The first camera 102A and the second camera 102B capture an image in synchronization.

In the target display period for which the target display operation is being performed, the area setting unit 216 sets a specific feature area A1 for a specific feature portion C1 of the specific target object M1. The specific feature portion C1 is a portion corresponding to the task feature portion C01 of the task target object M01. Here, the specific feature portion C1 of the specific target object M1 corresponds to the same portion as the task feature portion C01 of the task target object M01. Namely, in the specific target object M1, the contact portion in which one of the vertices of the equilateral triangle is brought into contact with the circumference of the circle corresponds to the specific feature portion C1. Furthermore, the area setting unit 216 sets comparison areas A2 to A4 in the rectangular region for the comparison target objects M2 to M4, respectively. Furthermore, the specific feature area A1 and the comparison areas A2 to A4 are not displayed on the display 101S. Furthermore, the shape of each of the specific feature area A1 and comparison areas A2 to A4 is not limited to a rectangle and the shape thereof may also be another shape, such as a circular shape, an elliptical shape, or a polygonal shape.

It is known that symptoms of cognitive functional impairment and brain functional impairment affect cognitive ability and memory ability of the subject. If the subject does not have cognitive functional impairment and brain functional impairment, after the subject viewed the instruction information I1 that is displayed on the display 101S in the instruction display operation, the subject attempts to memorize the shape of the task target object M01 by gazing at the task target object M01 indicated by the instruction information I1. Furthermore, if the subject does not have cognitive functional impairment and brain functional impairment, the subject is able to view the comparison target objects M2 to M4 one by one displayed on the display 101S in the target display operation, compare the task target object M01 memorized in the instruction display operation with the viewed comparison target objects M2 to M4, determine that these objects are not the same, finally find out the specific target object M1, and gaze at the found object. Furthermore, if the subject is not cognitive functional impairment and brain functional impairment, the subject tends to gaze at and memorize the task feature portion C01 of the task target object M01 in the instruction display operation, and make the determination by gazing the specific feature portion C1 of the specific target object M1 in the target display operation.

In contrast, if the subject has cognitive functional impairment and brain functional impairment, in the instruction display operation, the subject tends not to concentratedly view the task target object M01 by consecutively viewing the instruction information I1 or by alternately viewing the instruction information I1 and the task target object M01. Furthermore, if the subject has cognitive functional impairment and brain functional impairment, in some cases, the subject is not able to memorize the specific target object M1 in the instruction display operation or forgets the specific target object M1 immediately even if the subject memorizes the specific target object M1. Thus, it is difficult to make a comparison described above in the target display operation and, in some cases, the subject is not able to gaze at the specific target object M1.

Furthermore, in the target display operation, with a method for displaying the multiple target objects M1, M2, M3, and M4 on the display 101S, there may be a case in which, at the start of the target display operation, the gaze point P of the subject is accidentally placed at the specific target object M1 that is a correct answer. In such a case, since there is a possibility of determining that the subject found the correct answer regardless of whether the subject is cognitive functional impairment and brain functional impairment, it is difficult to evaluate the subject with high accuracy. Accordingly, for example, it is possible to evaluate the subject by performing the following processes.

First, as the instruction display operation, the display controller 202 displays the task target object M01 that includes the task feature portion C01 and the instruction information I1 on the display 101S. In this case, it is possible to evaluate the subject from a viewpoint whether, after the subject viewed the instruction information I1 displayed on the display 101S, the subject attempts to memorize the shape of the task target object M01 by gazing at the task feature portion C01 of the task target object M01 indicated by the instruction information I1. Furthermore, on the other hand, it is possible to evaluate the subject from a viewpoint, in the instruction display operation, whether the subject consecutively views the instruction information I1, whether the subject alternately views the instruction information I1 and the task target object M01, and whether the subject does not concentratedly view the task target object M01 and the task feature portion C01.

Furthermore, as the target display operation, it is assumed to be in a state in which the specific target object M1 and the multiple comparison target objects M2 to M4 are displayed on the display 101S. In this case, it is possible to evaluate the subject from a viewpoint whether the subject gazes at the multiple comparison target objects M2 to M4 one by one, whether the subject is able to finally reach the specific target object M1 that is a correct answer, how long does it take before the subject reaches the specific target object M1, and whether the subject is able to gaze at the specific feature portion C1 of the specific target object M1.

For example, in the instruction display operation, when a positional data of the gaze point P of the subject is detected, the determination unit 218 determines whether the gaze point P of the subject is present in the task feature area A and the instruction area B, and then, outputs determination data.

The arithmetic unit 220 calculates, based on the determination data, the gaze point transition data in the instruction display period that indicates the transition of the gaze point P in the instruction display period. The arithmetic unit 220 calculates, as the gaze point transition data in the instruction display period, the first presence time data, the second presence time data, the arrival time data in the instruction display period, and the movement frequency data in the instruction display period.

The first presence time data indicates a presence time in which the gaze point P is present in the task feature area A. In the embodiment, when the determination unit 218 determines whether the gaze point P is present in the task feature area A and the instruction area B at, for example, regular intervals, it is possible to estimate that the presence time in which the gaze point P is present in the task feature area A is longer as the number of determination that the gaze point P is present in the task feature area A is increased. Therefore, it is possible to use, as the first presence time data, the number of the determination that the gaze point P is present in the task feature area A by the determination unit 218. Namely, the arithmetic unit 220 is able to use a count value CNTA of the counter as the first presence time data.

The second presence time data indicates a presence time in which the gaze point P is present in the instruction area B. In the embodiment, when the determination unit 218 determines whether the gaze point P is present in the task feature area A and the instruction area B at, for example, regular intervals, it is possible to estimate that the presence time in which the gaze point P is present in the instruction area B is longer as the number of determination that the gaze point P is present in the instruction area B is increased. Therefore, it is possible to use, as the second presence time data, the number of the determination that the gaze point P is present in the instruction area B by the determination unit 218. Namely, the arithmetic unit 220 is able to use a count value CNTB of the counter as the second presence time data.

The arrival time data in the instruction display period indicates a period of time from a start time of the instruction display period to an arrival time at which the gaze point P first arrives at the task feature area A. Therefore, by measuring an elapsed time from the start of the instruction display period by the timer T1, and detecting a measurement value of the timer T1 when the gaze point P first arrives at the task feature area A with setting a flag value to 1, the arithmetic unit 220 is able to use a detection result of the timer T1 as the arrival time data in the instruction display period.

The movement frequency data in the instruction display period indicates the number of movement of the gaze point P between the task feature area A and the instruction area B. Therefore, the arithmetic unit 220 is able to count the number of movement of the gaze point P in the areas between the task feature area A and the instruction area B and use a count result as the movement frequency data in the instruction display period.

Regarding the instruction display operation, the evaluation unit 224 obtains evaluation data based on the first presence time data, the second presence time data, the arrival time data in the instruction display period, and the movement frequency data in the instruction display period.

Here, a data value based on the first presence time data is denoted by D11, a data value based on the second presence time data is denoted by D12, a data value based on the arrival time data in the instruction display period is denoted by D13, and a data value based on the movement frequency data in the instruction display period is denoted by D14. However, it is assumed that the data value D11 based on the first presence time data is the number of seconds in which the gaze point P is present in the task feature area A and, when the value thereof is greater than or equal to a predetermined upper limit a, a is set. Furthermore, it is assumed that the data value D12 based on the second presence time data is a value obtained by subtracting the number of seconds in which the gaze point P is present in the instruction area B from the above described value a. Furthermore, it is assumed that the data value D13 based on the arrival time data in the instruction display period is set to an inverse number of the arrival time (for example, 1/(arrival time)/10) (10 is a coefficient for setting an arrival time evaluation value to 1 or less based on an assumption that a minimum value of the arrival time is 0.1 second). Furthermore, it is assumed that the data value D14 based on the movement frequency data in the instruction display period is a value obtained by subtracting the count value from 1.

Furthermore, if the data value D14 is calculated, an upper limit may also be set to the count value that is subtracted from 1.

In this case, an evaluation value ANS may be represented, for example, as follows;

$$ANS1 = D11 \cdot K11 + D12 \cdot K12 + D13 \cdot K13 + D14 \cdot K14$$

K11 to K14 are constants for weighting. The constants K11 to K14 may be set appropriately.

A value of the evaluation value ANS1 represented by Expression above becomes large when the data value D11 based on the first presence time data is large, when the data value D12 based on the second presence time data is large, when the data value D13 based on the arrival time data in the instruction display period is large, and when the data value D14 based on the movement frequency data in the instruction display period is large. Namely, the evaluation value ANS1 becomes larger as the presence time of the gaze point P in the task feature area A is longer, as the presence time of the gaze point P in the instruction area B is shorter, as the arrival time at which the gaze point P arrives at the task feature area A after the start time of the instruction display period is shorter, and as the number of movement of the gaze point P between the task feature area A and the instruction area B is smaller.

In contrast, the value of the evaluation value ANS1 becomes smaller when the data value D11 based on the first presence time data is small, when the data value D12 based on the second presence time data is small, when the data value D13 based on the arrival time data in the instruction display period is small, and when the data value D14 based on the movement frequency data in the instruction display period is small. Namely, the evaluation value ANS1 becomes smaller as the presence time of the gaze point P in the task feature area A is shorter, as the presence time of the gaze point P in the instruction area B is longer, as the arrival time at which the gaze point P arrives at the task feature area A after the start time of the instruction display period is longer, and as the number of movement of the gaze point P between the task feature area A and the instruction area B is larger.

Therefore, the evaluation unit 224 is able to obtain the evaluation data by determining whether the evaluation value ANS1 is greater than or equal to a predetermined value. For example, when the evaluation value ANS1 is greater than or equal to the predetermined value, it is possible to evaluate that the subject is less likely to have cognitive functional impairment and brain functional impairment. Furthermore, when the evaluation value ANS1 is less than the predetermined value, it is possible to evaluate that the subject is highly likely to have cognitive functional impairment and brain functional impairment.

Furthermore, for example, when the positional data of the gaze point P of the subject is detected in the target display operation, the determination unit 218 determines whether the gaze point P of the subject is present in the specific feature area A1 and the multiple comparison areas A2 to A4, and outputs the determination data.

The arithmetic unit 220 calculates, based on the determination data, the gaze point transition data in the target display period that indicates the transition of the gaze point P in the target display period. The arithmetic unit 220 calculates, as the gaze point transition data in the target display period, the presence time data in the target display, the movement frequency data in the target display period, the final area data, and the arrival time data in the target display period.

The presence time data in the target display period indicates the presence time in which the gaze point P is present in the specific feature area A1. In the embodiment, when the determination unit 218 determines whether the gaze point P is present in the specific feature area A1 at, for example, regular intervals, it is possible to estimate that the presence time in which the gaze point P is present in the specific feature area A1 is longer as the number of determination that the gaze point P is present in the specific feature area A1 is increased. Therefore, it is possible to regard the presence time data in the target display period as the number of the determination by the determination unit 218 that the gaze point P is present in the specific feature area A1.

Namely, the arithmetic unit 220 is able to regard a count value CNTA1 of the counter as the presence time data in the target display period.

The movement frequency data in the target display period indicates the number of movement of the position of the gaze point P between the multiple comparison areas A2 to A4 before the gaze point P first arrives at the specific feature area A1. Therefore, the arithmetic unit 220 is able to count the number of movement of the gaze point P in the areas between the specific feature area A1 and the comparison areas A2 to A4 and use the count result before the gaze point P arrives at the specific feature area A1 as the movement frequency data in the target display period.

Furthermore, the final area data indicates an area in which the gaze point P is finally present among the specific feature area A1 and the comparison areas A2 to A4 in the target display period, i.e., an area that is gazed at by the subject as the answer. The arithmetic unit 220 updates the area in which the gaze point P is present every time the gaze point P is detected and is thus able to use the detection result at the end of the target display period as the final area data.

Furthermore, the arrival time data in the target display period indicates a period of time from a start time of the target display period to an arrival time at which the gaze point P first arrives at the specific feature area A1. Therefore, by measuring an elapsed time from the start of the target display period by the timer T1, and detecting a measurement value of the timer T1 when the gaze point P first arrives at the specific feature area A1 with setting a flag value to 1, the arithmetic unit 220 is able to use a detection result the timer T1 as the arrival time data in the target display period.

Regarding the target display operation, the evaluation unit 224 obtains the evaluation data based on the presence time data in the target display period, the movement frequency data in the target display period, the final area data, and the arrival time data in the target display period.

Here, a data value based on the final area data is denoted by D21, a data value based on the presence time data in the target display period is denoted by D22, a data value based on the arrival time data in the target display period is denoted by D23, and a data value based on the movement frequency data in the target display period is denoted by D24. However, the data value D21 based on the final area data is set to 1 if the gaze point P of the subject is finally present in the specific feature area A1 (i.e., in a case of a correct answer), and set to 0 if the gaze point P of the subject is finally not present in the specific feature area A1 (i.e., in a case of an incorrect answer). Furthermore, it is assumed that the data value D22 based on the presence time data in the target display period is the number of seconds in which the gaze point P is present in the specific feature area A1. Furthermore, regarding the data value D22, it may also be possible to set an upper limit value that is a smaller number of seconds than the display period. Furthermore, the data value D23 based on the arrival time data in the target display period is set to an inverse number of the arrival time (for example, 1/(arrival time)/10) (10 is a coefficient for setting an arrival time evaluation value to 1 or less based on an assumption that a minimum value of the arrival time is 0.1 second). Furthermore, the count value is used as it is as the data value D24 based on the movement frequency data in the target display period. Furthermore, it may also be possible to appropriately set an upper limit value for the data value D24.

In this case, the evaluation value ANS is able to be represented, for example, as follows;

$$ANS2 = D21 \cdot K21 + D22 \cdot K22 + D23 \cdot K23 + D24 \cdot K24$$

K21 to K24 are constants for weighting. The constants K21 to K24 may be appropriately set.

A value of the evaluation value ANS2 represented by Expression above becomes large when the data value D21 based on the final area data is set to 1, when the data value D22 based on the presence time data in the target display period is large, when the data value D23 based on the arrival time data in the target display period is large, and when the value of the data value D24 based on the movement frequency data in the target display period is large. Namely, the evaluation value ANS2 becomes larger when the gaze point P is finally present in the specific feature area A1, when the presence time of the gaze point P in the specific feature area A1 is longer, when the arrival time at which the gaze point P arrives at the specific feature area A1 after the start time of the target display period is shorter, and when the number of movement of the gaze point P among the individual areas is larger.

In contrast, the value of the evaluation value ANS2 becomes smaller when the data value D21 based on the final area data is 0, when the data value D22 based on the presence time data in the target display period is small, when the data value D23 based on the arrival time data in the target display period is small, and when the data value D24 based on the movement frequency data in the target display period is small. Namely, the evaluation value ANS2 becomes smaller when the gaze point P is finally not present in the specific feature area A1, when the presence time of the gaze point P in the specific feature area A1 is shorter, when the arrival time at which the gaze point P arrives at the specific feature area A1 after the start time of the target display period is longer, and when the number of movement of the gaze point P among the areas is smaller.

Therefore, the evaluation unit 224 is able to obtain the evaluation data by determining whether the evaluation value ANS2 is greater than or equal to the predetermined value. For example, when the evaluation value ANS2 is greater than or equal to the predetermined value, it is possible to evaluate that the subject is less likely to have cognitive functional impairment and brain functional impairment. Furthermore, when the evaluation value ANS2 is less than the predetermined value, it is possible to evaluate that the subject is highly likely to have cognitive functional impairment and brain functional impairment.

Furthermore, the evaluation unit 224 is able to store the evaluation value ANS2 in the storage 222. For example, it may also be possible to cumulatively store the evaluation value ANS2 for the same subject and perform evaluation by comparing with the past evaluation values. For example, when the evaluation value ANS2 is higher than the past evaluation value, it is possible to evaluate that a cognitive function and a brain function have improved. Furthermore, when a cumulative value of the evaluation value ANS2 is gradually increased, it is possible to evaluate that the cognitive function and the brain function have gradually improved.

Furthermore, the evaluation unit 224 may also be able to perform evaluation by using the presence time data in the target display period, the movement frequency data in the target display period, the final area data, and the arrival time data in the target display period individually or in combination. For example, when the gaze point P accidentally arrives at the specific feature area A1 while the multiple target objects are viewed, the data value D24 based on the movement frequency data in the target display period becomes small. In this case, it is possible to perform evaluation together with the data value D22 based on the presence time data in the target display period described above. For example, when the number of movement is small but the presence time is long, it is possible to evaluate that the subject can gaze at the specific feature area A1 that is a correct answer. Furthermore, when the number of movement is small and the presence time is also short, it is possible to evaluate that the gaze point P has accidentally passed through the specific feature area A1.

Furthermore, when the number of movement is small and the final area is the specific feature area A1, it is possible to evaluate that, for example, the gaze point P arrives at the specific feature area A1 that is the correct answer with a smaller number of movement. In contrast, when the number of movement described above is small and the final area is not the specific feature area A1, it is possible to evaluate that, for example, the gaze point P has accidentally passed through the specific feature area A1.

Furthermore, the evaluation unit 224 may also be possible to perform evaluation by using, in combination, the evaluation value ANS1 in the instruction display operation and the evaluation value ANS2 in the target display operation.

In the embodiment, when the evaluation unit 224 outputs the evaluation data, the output controller 226 is able to allow the output device 50 to output, in accordance with the evaluation data, character data indicating that, for example, "it seems that the subject is less likely to have cognitive functional impairment and brain functional impairment" or character data indicating that "it seems that the subject is highly likely to have cognitive functional impairment and brain functional impairment". Furthermore, when the evaluation value ANS for the same subject becomes higher than the past evaluation value ANS, the output controller 226 is able to allow the output device 50 to output character data indicating that "a cognitive function and a brain function have improved" or the like.

Figure 10:
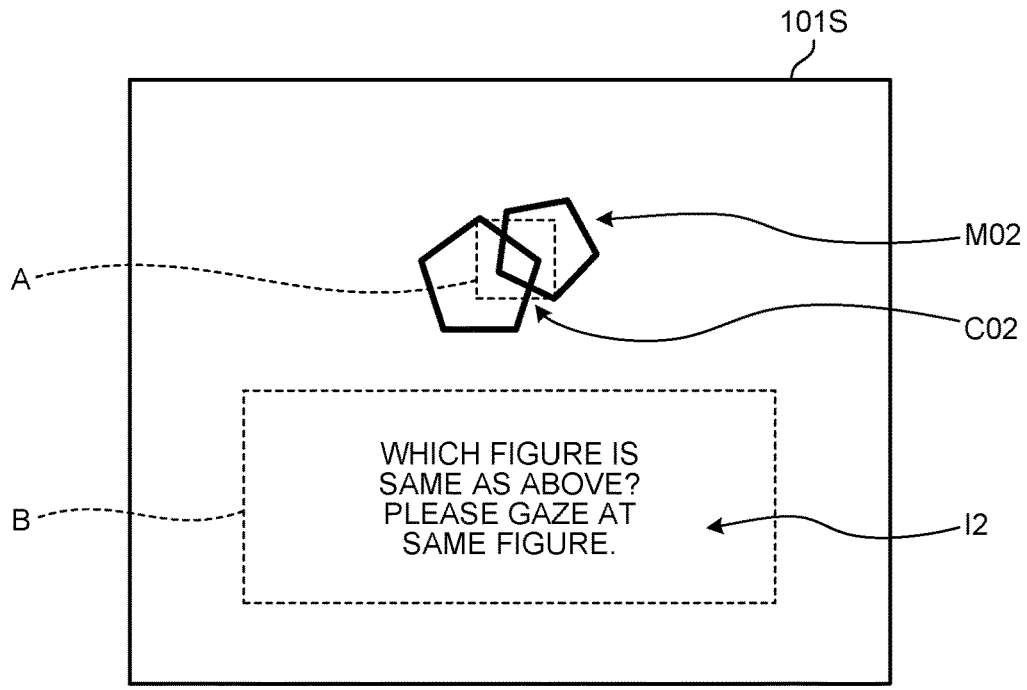
FIG. 10 is a diagram illustrating another example of content that is displayed on the display in the instruction display operation.

FIG. 10 is a diagram illustrating another example of content displayed on the display 101S in the instruction display operation. As illustrated in FIG. 10, the display controller 202 simultaneously displays, in the instruction display operation, a task target object M02 on the display 101S and instruction information 12 for instructing the subject to gaze at the same figure as the task target object M02 on the display 101S. The task target object M02 is a pattern that is formed by multiple same shapes (for example, a pentagon). Specifically, the task target object M02 has a shape of a combination of two pentagons, and one of the corner portions of the one pentagon overlaps with that of the other pentagon. In the task target object M02, the overlapping portion in which one of the corner portions of the one pentagon overlaps with that of the other pentagon is a portion that can be an appearance feature when the subject memorizes the portion, i.e., the task feature portion C02.

The area setting unit 216 sets a task feature area A in the rectangular region that includes, for example, the task feature portion C02 of the task target object M02. Furthermore, the area setting unit 216 sets an instruction area B in the rectangular region that includes, for example, the instruction information 12. The area setting unit 216 sets the task feature area A and the instruction area B on the display 101S such that the areas do not overlap with each other.

Figure 11:
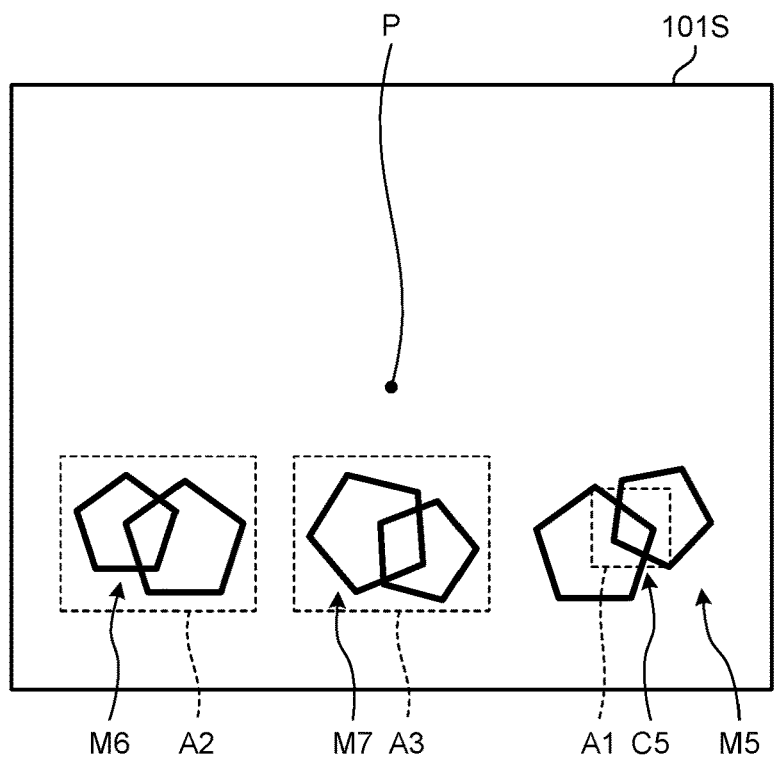
FIG. 11 is a diagram illustrating another example of a case in which multiple target objects are displayed on the display in the target display operation.

FIG. 11 is a diagram illustrating another example of a case in which multiple target objects are displayed on the display 101S in the target display operation. After the instruction display operation, the display controller 202 displays, in the target display operation, as illustrated in FIG. 11, a specific target object M5 that is a correct answer to the instruction information 12 and the comparison target objects M6 and M7 that are incorrect answers to the instruction information 12.

Similarly to the above description, based on a content of the instruction information 12, the task target object M02 and the specific target object M5 are the same target objects in appearance. Therefore, similarly to the task target object M02, the specific target object M5 has a shape of a combination of two pentagons and one of the corner portions of the one pentagon overlaps that of the other pentagon. Furthermore, similarly to the specific target object M5, the comparison target objects M6 and M7 each have a shape of a combination of two pentagons. However, each of the comparison target objects M6 and M7 has a shape in which the corner portions that are different from those in the specific target object M5 overlap with each other.

The area setting unit 216 is able to set a specific feature area A1 for a specific feature portion C5 of the specific target object M5 and is able to set comparison areas A2 and A3 for the comparison target objects M6 and M7, respectively. The specific feature portion C5 corresponds to a portion for the task feature portion C02 of the task target object M02. Here, the specific feature portion C5 of the specific target object M5 corresponds to the same portion as the task feature portion C02 of the task target object M02. Namely, in the specific target object M5, the overlapping portion in which one of the corner portions of the one pentagon overlaps with that of the other pentagon is the specific feature portion C5. The area setting unit 216 sets the specific feature area A1 and the comparison areas A2 and A3 on the display 101S so as not to overlap with each other. In this way, in the target display operation, by displaying the specific target object M5 and the comparison target objects M6 and M7 that are similar figures, it is also possible to perform evaluation related to a figure recognition function of the subject.

Figure 12:
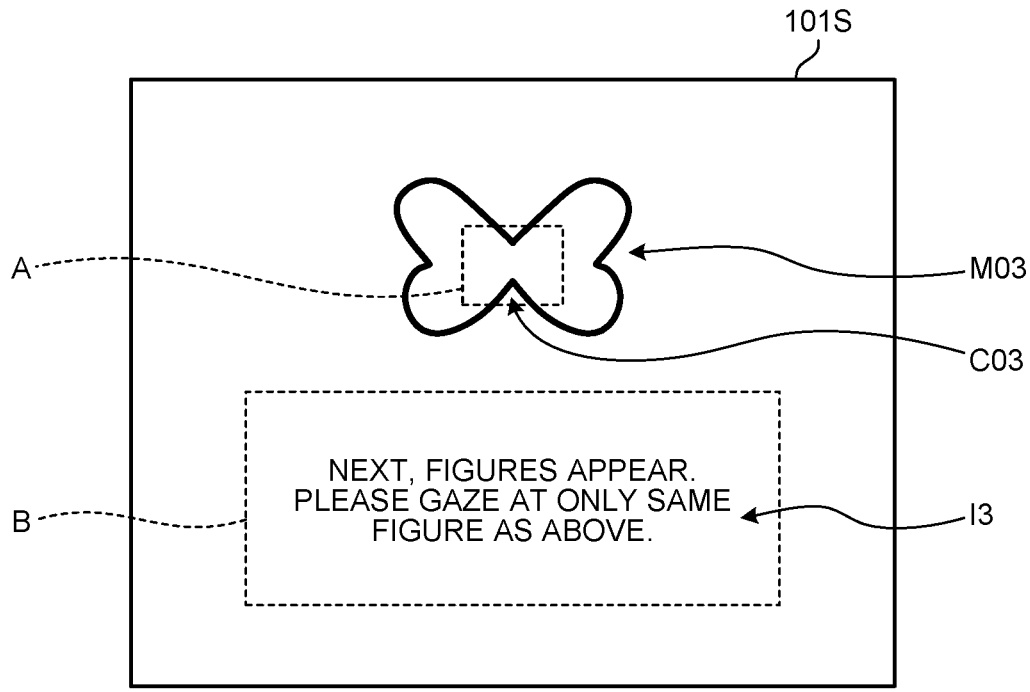
FIG. 12 is a diagram illustrating another example of content that is displayed on the display in the instruction display operation.

FIG. 12 is a diagram illustrating another example of the content that is displayed on the display 101S in the instruction display operation. As illustrated in FIG. 12, in the instruction display operation, the display controller 202 simultaneously displays a task target object M03 on the display 101S and instruction information 13 for instructing the subject to gaze at the same figure as the task target object M03 on the display 101S. The task target object M03 is a pattern that is obtained by bilaterally and symmetrically arranging two heart shapes each of which is rotated by, for example, 90° and deleting lines of an overlapping portion from a shape in which each of protruding end portions overlaps. In this case, the overlapping portion of the two heart shapes corresponds to a recess portion in appearance. In the task target object M03, this kind of recess portion can be an appearance feature when the subject memorizes the portion, i.e., the task feature portion C03.

The area setting unit 216 sets a task feature area A in the rectangular region that includes, for example, the task feature portion C03 of the task target object M03. Furthermore, the area setting unit 216 sets an instruction area B in the rectangular region that includes, for example, the instruction information 13. The area setting unit 216 sets the task feature area A and the instruction area B on the display 101S such that these areas do not overlap with each other.

Figure 13:
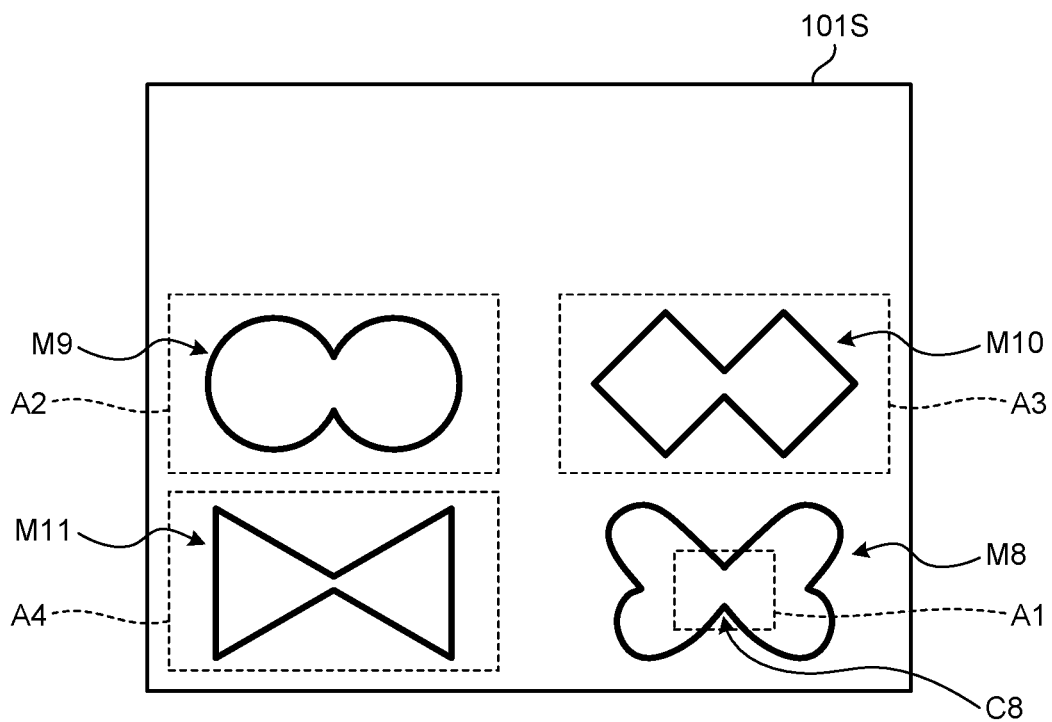
FIG. 13 is a diagram illustrating another example of a case in which multiple target objects are displayed on the display in the target display operation.

FIG. 13 is a diagram illustrating another example in a case in which multiple target objects are displayed on the display 101S in the target display operation. After the instruction display operation, as illustrated in FIG. 13, the display controller 202 displays, in the target display operation, a specific target object M8 that is a correct answer to the instruction information 13 and the comparison target objects M9 to M11 that is incorrect answers to the instruction information 13.

Similarly to the above description, based on the content of the instruction information 13, the task target object M03 and the specific target object M8 are the same target object in appearance. Therefore, similarly to the task target object M03, the specific target object M8 is a pattern that is obtained by bilaterally and symmetrically arranging two heart shapes each of which is rotated by, for example, 90° and deleting the lines of the overlapping portion from the shape in which each of the protruding end portions overlaps. Furthermore, similarly to the specific target object M8, the comparison target objects M9 to M11 are patterns each of which is obtained by deleting the lines of the overlapping portion from the shape that is obtained by bilaterally and symmetrically arranging two figures. The comparison target object M9 is a pattern based on circles, the comparison target object M10 is a pattern based on quadrilaterals, the comparison target object M11 is a pattern based on triangles.

The area setting unit 216 is able to set a specific feature area A1 for a specific feature portion C8 of the specific target object M8 and is able to set comparison areas A2 to A4 for the comparison target objects M9 to M11 respectively. The specific feature portion C8 corresponds to a portion for the task feature portion C03 of the task target object M03. Here, the specific feature portion C8 of the specific target object M8 corresponds to the same portion as the task feature portion C03 of the task target object M03. Namely, in the specific target object M8, the recess portion that is formed by the overlapping portion of the two heart shapes corresponds to the specific feature portion C8. The area setting unit 216 sets the specific feature area A1 and the comparison areas A2 to A4 on the display 101S such that these areas do not overlap with each other. In this way, in the target display operation, by displaying the specific target object M8 and the comparison target objects M9 to M11 that are similar figures, it is possible to evaluate a figure recognition function of the subject.

Figure 14:
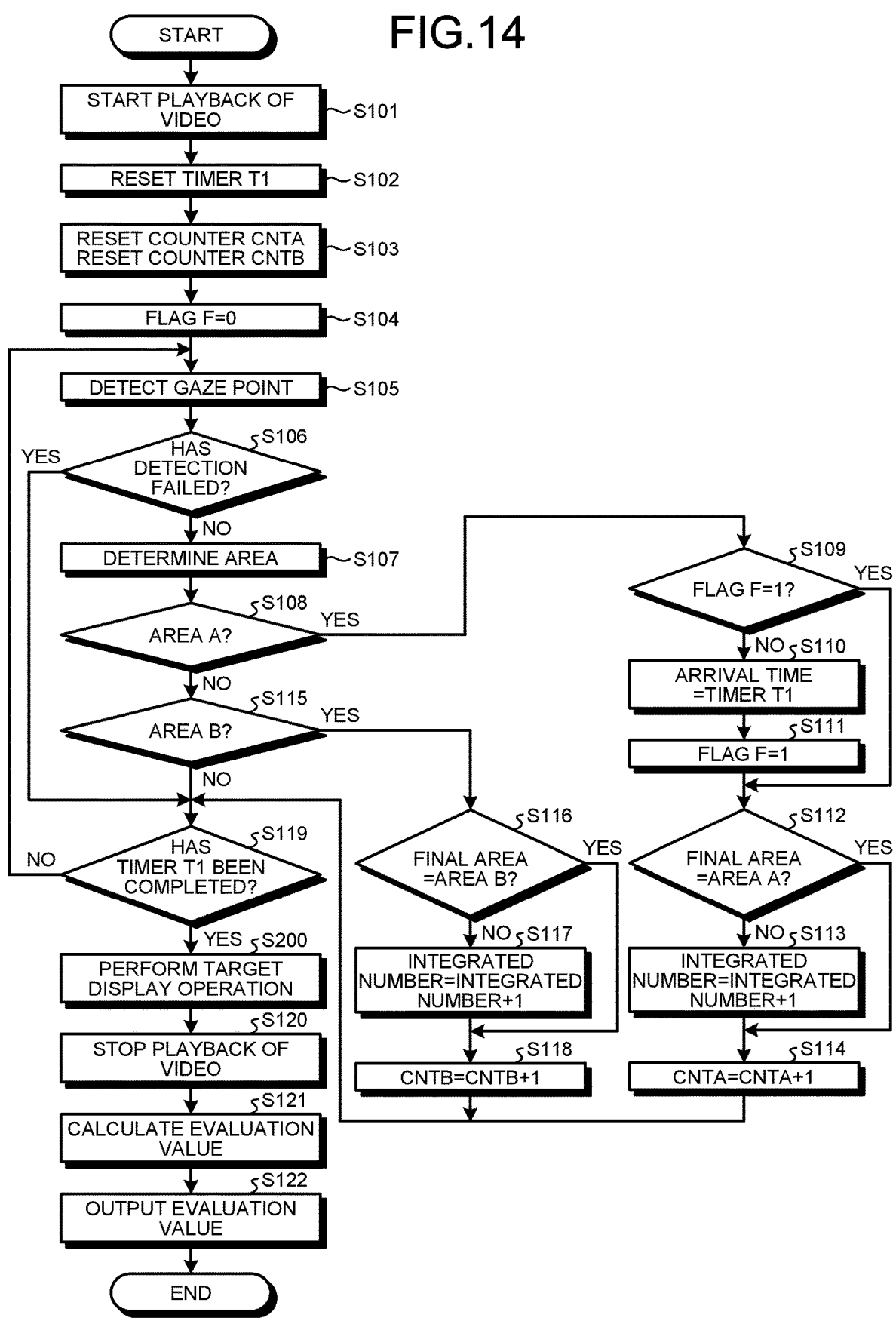
FIG. 14 is a flowchart illustrating an example of an evaluation method.
Figure 15:
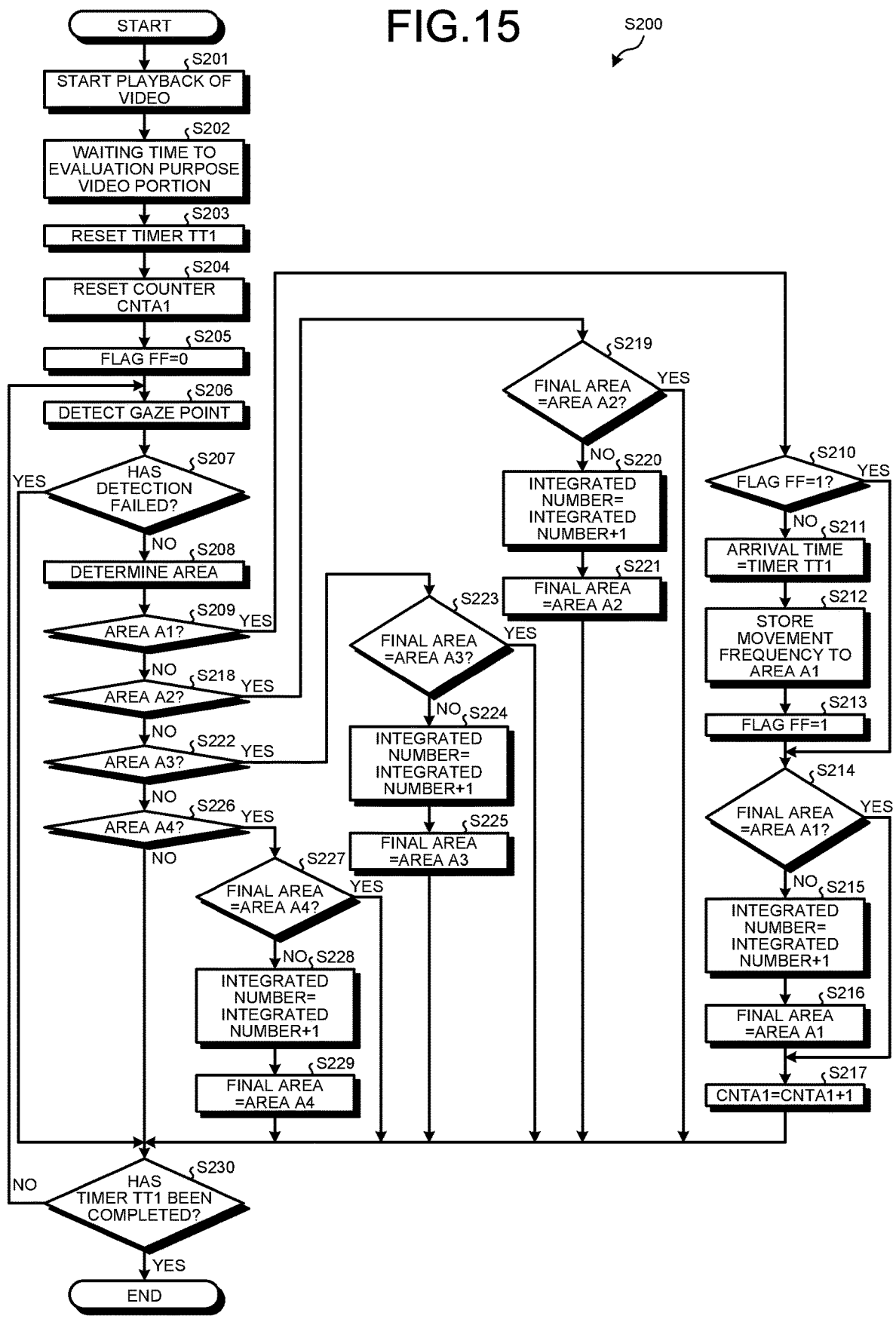
FIG. 15 is a flowchart illustrating an example of an evaluation method in the target display operation.

In the following, an example of the evaluation method according to the embodiment will be described. FIG. 14 and FIG. 15 are flowcharts each illustrating an example of the evaluation method according to the embodiments. In the embodiments, a description will be given of an example of the evaluation method in a case in which the instruction display operation and the target display operation are consecutively performed. An example of the instruction display operation is mainly illustrated in FIG. 14 and an example of the target display operation is illustrated in FIG. 15.

As illustrated in FIG. 14, in the instruction display operation, the display controller 202 starts a playback of a video (Step S101), and then, resets the timer T1 (Step S102), resets count values CNTA and CNTB of the counter (Step S103), and sets a flag value F to zero (Step S104).

The gaze point detecting unit 214 detects a positional data of the gaze point P of the subject on the display 101S of the display device 101 for each defined sampling period (for example, 20 (msec)) while showing the video displayed on the display device 101 to the subject (Step S105). When the positional data has been detected (No at Step S106), the determination unit 218 determines, based on the positional data, the area in which the gaze point P is present (Step S107). Furthermore, when the positional data is not detected (Yes at Step S106), the process at Step S119 and the subsequent processes, which will be described later, are performed.

When it is determined that the gaze point P is present in the task feature area A (Yes at Step S108), the arithmetic unit 220 determines whether the flag value F is 1, i.e., whether the gaze point P arrives at the task feature area A for the first time (1: has already arrived, 0: has not arrived yet) (Step S109). When the flag value F is 1 (Yes at Step S109), the arithmetic unit 220 skips the subsequent processes at Step S110 and Step S111 and performs the process at Step S112 that will be described later.

Furthermore, when the flag value F is not 1, i.e., the gaze point P arrives at the task feature area A for the first time (No at Step S109), the arithmetic unit 220 extracts the measurement result of the timer T1 as the arrival time data in the instruction display period (Step S110). After that, the arithmetic unit 220 changes the flag value to 1 (Step S111).

Then, the arithmetic unit 220 determines whether the area in which the gaze point P is present at the latest detection, i.e., the final area, is the task feature area A (Step S112). When the arithmetic unit 220 determines that the final area is the task feature area A (Yes at Step S112), the arithmetic unit 220 skips the subsequent process at Step S113 and performs the process at Step S114 that will be described later. Furthermore, when it is determined that the final area is not the task feature area A (No at Step S112), the arithmetic unit 220 increments an integrated number that indicates the number of movement of the gaze point P among the areas by 1 (Step S113), and increments the count value CNTA that indicates the first presence time data in the task feature area A by 1 (Step S114). After that, the arithmetic unit 220 performs the process at Step S119 and the subsequent processes that will be described later.

Furthermore, when it is determined that the gaze point P is not present in the task feature area A (No at Step S108), the arithmetic unit 220 determines whether the gaze point P is present in the instruction area B (Step S115). When it is determined that the gaze point P is present in the instruction area B (Yes at Step S115), the arithmetic unit 220 determines whether the area in which the gaze point P is present at the latest detection, i.e., the final area, is the instruction area B (Step S116). When the arithmetic unit 220 determines that the final area is the instruction area B (Yes at Step S116), the arithmetic unit 220 skips the subsequent process at Step S117 and performs the process at Step S118 that will be described later. Furthermore, when it is determined that the final area is not the instruction area B (No at Step S116), the arithmetic unit 220 increments an integrated number that indicates the number of movement of the gaze point P among the areas by 1 (Step S117), and increments the count value CNTB that indicates the second presence time data in the instruction area B by 1 (Step S118). After the process at Step S118, and when it is determined that the gaze point P is not present in the instruction area B at the process at Step S115 (No at Step S115), the arithmetic unit 220 performs the process at Step S119 and the subsequent processes that will be described later.

After that, the arithmetic unit 220 determines, based on the detection result of the detection timer T1, whether the time reaches a completion time of the playback of the video (Step S119). When it is determined, by the arithmetic unit 220, that the time does not reach the completion time of the playback of the video (No at Step S119), the arithmetic unit 220 repeatedly performs the process at Step S105 and the subsequent processes described above.

When it is determined, by the arithmetic unit 220, that the time reaches the completion time of the playback of the video (Yes at Step S119), the target display operation is performed (Step S200). As illustrated in FIG. 15, in the target display operation, the display controller 202 starts a playback of a video (Step S201). After an elapse of a waiting time to an evaluation purpose video portion (Step S202), the display controller 202 resets a timer TT1 (Step S203), resets a count value CNTA1 of the counter (Step S204), and sets a flag value FF to 0 (Step S205).

The gaze point detecting unit 214 detects a positional data of the gaze point P of the subject on the display 101S of the display device 101 for each defined sampling period (for example, 20 (msec)) while showing the video displayed on the display device 101 to the subject (Step S206). When the positional data is not detected (Yes at Step S207), the arithmetic unit 220 performs the process at Step S230 and the subsequent processes that will be described later. When the positional data has been detected (No at Step S207), the determination unit 218 determines, based on the positional data, the area in which the gaze point P is present (Step S208).

When it is determined that the gaze point P is present in the specific feature area A1 (Yes at Step S209), the arithmetic unit 220 determines whether the flag value FF is 1, i.e., whether the gaze point P arrives at the specific feature area A1 for the first time (1: has already arrived, 0: has not arrived yet) (Step S210). When the flag value FF is 1 (Yes at Step S210), the arithmetic unit 220 skips the subsequent processes at Step S211 to Step S213 and performs the process at Step S214 that will be described later.

Furthermore, when the flag value FF is not 1, i.e., when the gaze point P arrives at the specific feature area A1 for the first time (No at Step S210), the arithmetic unit 220 extracts the measurement result of the timer TT1 as the arrival time data in the target display period (Step S211). Furthermore, the arithmetic unit 220 allows the storage 222 to store the movement frequency data in the target display period that indicates the number of movement of the gaze point P among the areas before the gaze point P arrives at the specific feature area A1 (Step S212). After that, the arithmetic unit 220 changes the flag value FF to 1 (Step S213).

Then, the arithmetic unit 220 determines whether the area in which the gaze point P is present at the latest detection, i.e., the final area, is the specific feature area A1 (Step S214). When the arithmetic unit 220 determines that the final area is the specific feature area A1 (Yes at Step S214), the arithmetic unit 220 skips the processes at Step S215 and Step S216 and performs the process at Step S217 and the subsequent processes that will be described later. Furthermore, when it is determined that the final area is not the specific feature area A1 (No at Step S214), the arithmetic unit 220 increments an integrated number that indicates the number of movement of the gaze point P among the areas by 1 (Step S215), and changes the final area to the specific feature area A1 (Step S216). Furthermore, the arithmetic unit 220 increments the count value CNTA1 that indicates the presence time data in the target display period in the specific feature area A1 by 1 (Step S217). After that, the arithmetic unit 220 performs the process at Step S230 and the subsequent processes that will be described later.

Furthermore, when it is determined that the gaze point P is not present in the specific feature area A1 (No at Step S209), the arithmetic unit 220 determines whether the gaze point P is present in the comparison area A2 (Step S218). When it is determined that the gaze point P is present in the comparison area A2 (Yes at Step S218), the arithmetic unit 220 determines whether the area in which the gaze point P is present at the latest detection, i.e., the final area, is the comparison area A2 (Step S219). When the arithmetic unit 220 determines that the final area is the comparison area A2 (Yes at Step S219), the arithmetic unit 220 skips the subsequent processes at Step S220 and Step S221 and performs the process at Step S230 that will be described later. Furthermore, when it is determined that the final area is not the comparison area A2 (No at Step S219), the arithmetic unit 220 increments an integrated number that indicates the number of movement of the gaze point P among the areas by 1 (Step S220), and changes the final area to the comparison area A2 (Step S221). After that, the arithmetic unit 220 performs the process at Step S230 and the subsequent processes which will be described later.

Furthermore, when it is determined that the gaze point P is not present in the comparison area A2 (No at Step S218), the arithmetic unit 220 determines whether the gaze point P is present in the comparison area A3 (Step S222). When it is determined that the gaze point P is present in the comparison area A3 (Yes at Step S222), the arithmetic unit 220 determines whether the area in which the gaze point P is present at the latest detection, i.e., the final area, is the comparison area A3 (Step S223). When the arithmetic unit 220 determines that the final area is the comparison area A3 (Yes at Step S223), the arithmetic unit 220 skips the subsequent processes at Step S224 and Step S225 and performs the process at Step S230 that will be described later. Furthermore, when it is determined that the final area is not the comparison area A3 (No at Step S223), the arithmetic unit 220 increments an integrated number that indicates the number of movement of the gaze point P among the areas by 1 (Step S224), and changes the final area to the comparison area A3 (Step S225). After that, the arithmetic unit 220 performs the process at Step S230 and the subsequent processes that will be described later.

Furthermore, when it is determined that the gaze point P is not present in the comparison area A3 (No at Step S222), the arithmetic unit 220 determines whether the gaze point P is present in the comparison area A4 (Step S226). When it is determined that the gaze point P is present in the comparison area A4 (Yes at Step S226), the arithmetic unit 220 determines whether the area in which the gaze point P is present at the latest detection, i.e., the final area, is the comparison area A4 (Step S227). When the arithmetic unit 220 determines that the final area is the comparison area A4 (Yes at Step S227), the arithmetic unit 220 skips the subsequent processes at Step S228 and Step S229 and performs the process at Step S230 that will be described later. Furthermore, when it is determined that the final area is not the comparison area A4 (No at Step S227), the arithmetic unit 220 increments an integrated number that indicates the number of movement of the gaze point P among the areas by 1 (Step S228), and changes the final area to the comparison area A4 (Step S229). After the process at Step S229, and when it is determined, at Step S226, that the gaze point P is not present in the comparison area A4 (No at Step S226), the arithmetic unit 220 performs the process at Step S230 and the subsequent processes that will be described later.

After that, the arithmetic unit 220 determines, based on the detection result of the detection timer TT1, whether the time reaches a completion time of the playback of the video (Step S230). When it is determined, by the arithmetic unit 220, that the time does not reach the completion time of the playback of the video (No at Step S230), the arithmetic unit 220 repeatedly performs the process at Step S206 and the subsequent processes described above.

When it is determined, by the arithmetic unit 220, that the time reaches the completion time of the playback of the video (Yes at Step S230), the target display operation has been completed. After the completion of the target display operation, as illustrated in FIG. 14, the display controller 202 stops the playback of the video for the instruction display operation (Step S120). After the playback of the video is stopped, the evaluation unit 224 calculates the evaluation value that is obtained from the processing result described above, and obtains evaluation data based on the evaluation value (Step S121). At Step S121, the evaluation unit 224 calculates the evaluation value ANS1 based on, for example, the first presence time data, the second presence time data, the movement frequency data in the instruction display period, and the arrival time data in the instruction display period that are obtained from the processing result in the instruction display operation (Step S121), and obtains the evaluation data based on the evaluation value ANS1. Furthermore, the evaluation unit 224 calculates the evaluation value ANS2 based on, for example, the presence time data in the target display period, the movement frequency data in the target display period, the final area data, and the arrival time data in the target display period that are obtained from the processing result in the target display operation (Step S121), and obtains the evaluation data based on the evaluation value ANS2. After that, the output controller 226 outputs the evaluation data by the evaluation unit 224 (Step S122). Furthermore, in the example described above, a case in which the evaluation data is output after the instruction display operation and the target display operation are consecutively performed has been described. However, the case is not limited to this and it may also be possible to perform an evaluation every time each of the instruction display operation and the target display operation has been completed.

Furthermore, in the embodiment described above, a description has been given with a case, as an example, in which the area setting unit 216 sets, in the target display operation, the specific feature area A1 in the specific feature area of the specific target object. In contrast, in the target display operation, the area setting unit 216 may also set the specific feature area A1 for the specific feature area of the specific target object and a specific area for an entirety of the specific target object.

Figure 16:
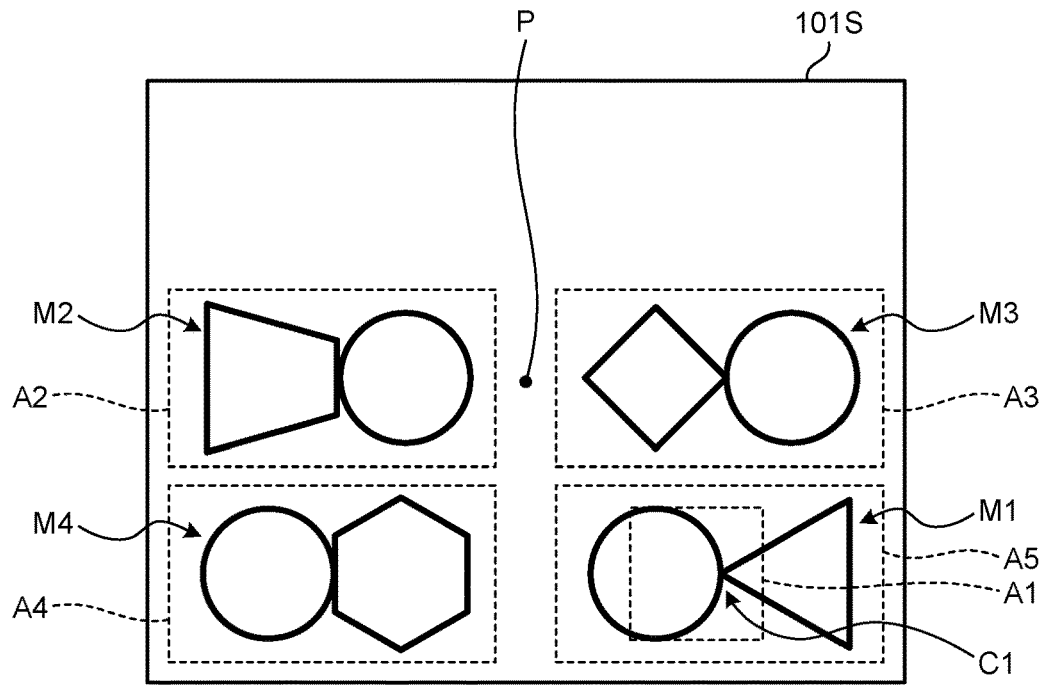
FIG. 16 is a diagram illustrating another example of a case in which multiple target objects are displayed on the display in the target display operation.
Figure 17:
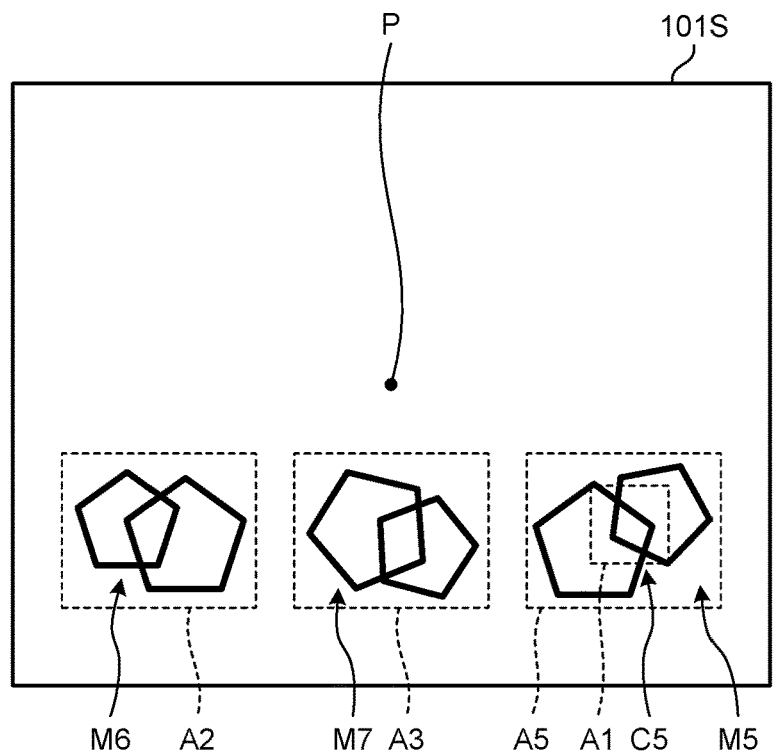
FIG. 17 is a diagram illustrating another example of a case in which multiple target objects are displayed on the display in the target display operation.
Figure 18:
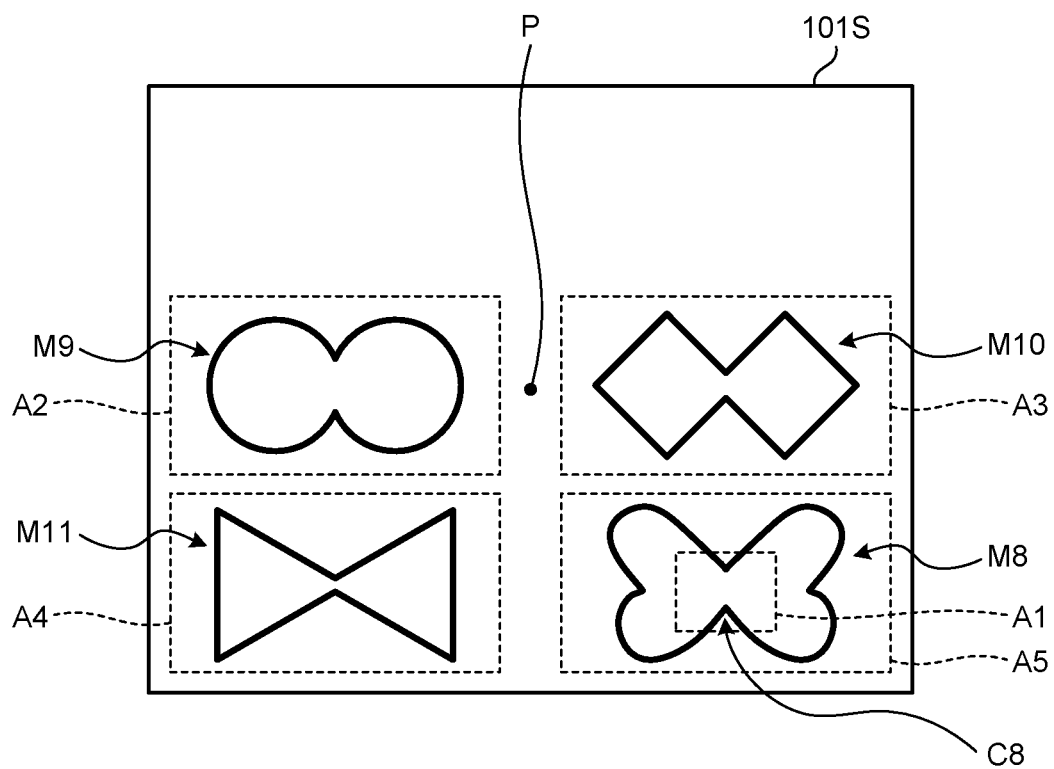
FIG. 18 is a diagram illustrating another example of a case in which multiple target objects are displayed on the display in the target display operation.

FIG. 16 to FIG. 18 are diagrams each illustrating an example of a case in which, in the respective target display operations illustrated in FIG. 9, FIG. 11, and FIG. 13, a specific area for an entirety of the specific target object is set in addition to the specific feature area A1 for the specific feature area of the specific target object. As illustrated in FIG. 16, an area setting unit 215 is able to set, in the target display operation, a specific area A5 in the rectangular region for an entirety of the specific target object M1 in addition to the specific feature area A1 for the specific feature portion C1 of the specific target object M1. Furthermore, as illustrated in FIG. 17, the area setting unit 215 is able to set, in the target display operation, a specific area A5 in the rectangular region for an entirety of the specific target object M5 in addition to the specific feature area A1 for the specific feature portion C5 of the specific target object M5. Furthermore, as illustrated in FIG. 18, the area setting unit 215 is able to set, in the target display operation, a specific area A5 in the rectangular region for an entirety of the specific target object M8 in addition to the specific feature area A1 for the specific feature portion C8 of the specific target object M8. Furthermore, the shape of each of the specific areas A5 illustrated in FIG. 16 to FIG. 18 is not limited to a rectangle and may also be another shape, such as a circular shape, an elliptical shape, or a polygonal shape.

Figure 19:
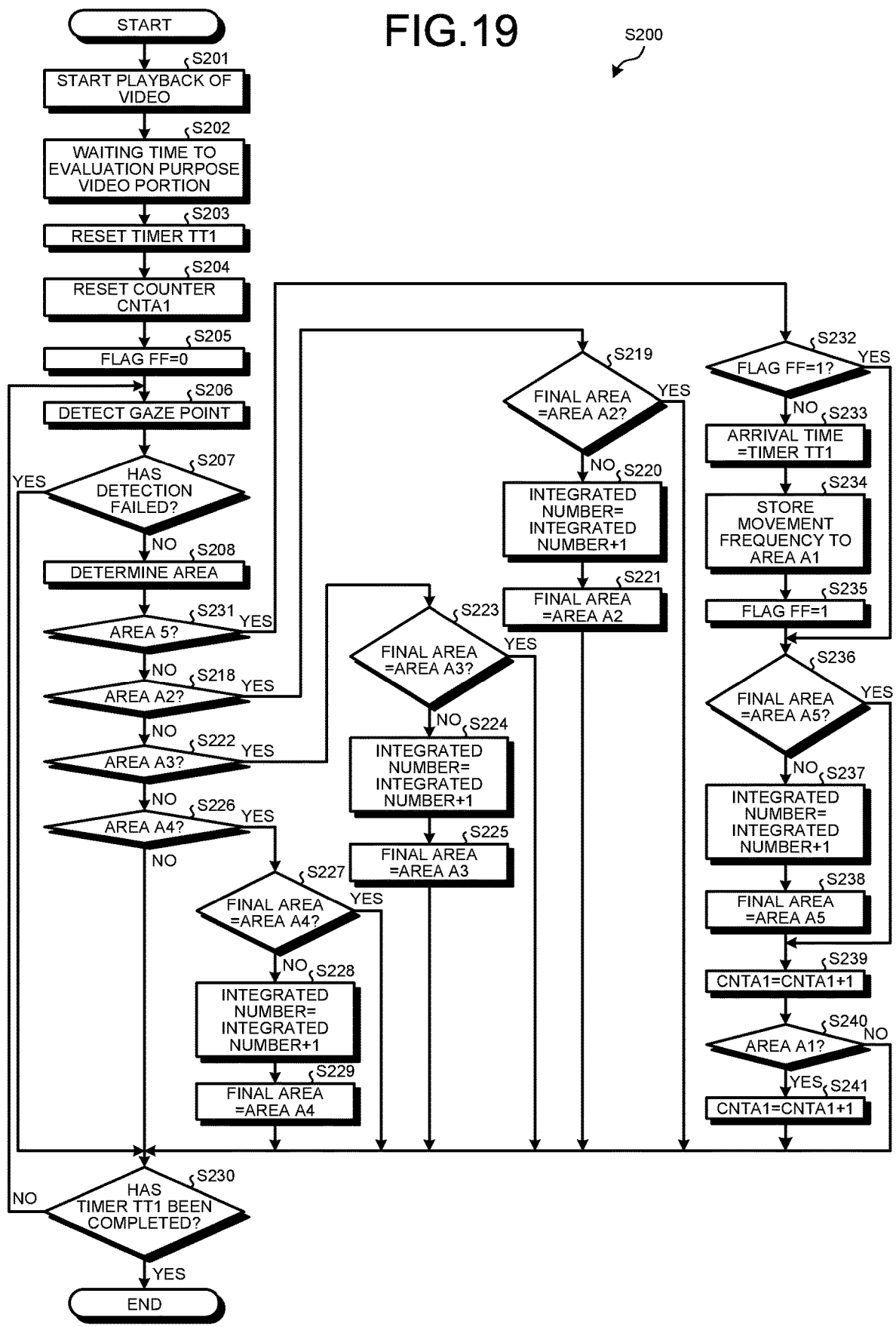
FIG. 19 is a flowchart illustrating another example of the evaluation method in the target display operation.

FIG. 19 is a flowchart illustrating another example of the evaluation method according to the embodiments. FIG. 19 illustrates an operation of performing, in the target display operation, a determination in a case in which a specific area for the entirety of the specific target object is set in addition to the specific feature area A1 for the specific feature area of the specific target object.

As illustrated in FIG. 19, similarly to the embodiments described above, the display controller 202 starts, in the target display operation, a playback of a video (Step S201). After the elapse of the waiting time to the evaluation purpose video portion (Step S202), the display controller 202 resets the timer TT1 (Step S203), resets the count value CNTA1 of the counter (Step S204), and sets the flag value FF to 0 (Step S205). The gaze point detecting unit 214 detects the positional data of the gaze point P of the subject on the display 101S of the display device 101 (Step S206). When the positional data is detected (No at Step S207), the determination unit 218 determines, based on the positional data, the area in which the gaze point P is present (Step S208).

In the embodiments described above, a determination whether or not the gaze point P is present in the specific feature area A1 has been performed. However, here, a determination whether or not the gaze point P is present in the specific area A5 is performed (Step S231). When it is determined that the gaze point P is not present in the specific area A5 (No at Step S231), similarly to the embodiments described above, the process at Step S218 and the subsequent processes are performed. In this case, the content of the process at Step S218 and the subsequent processes is the same as that described in the embodiments above.

In contrast, when it is determined that the gaze point P is present in the specific area A5 (Yes at Step S231), the arithmetic unit 220 determines whether the flag value FF is 1, i.e., whether the gaze point P arrives at specific area A5 for the first time (1: has already arrived, 0: has not arrived yet) (Step S232). When the flag value FF is 1 (Yes at Step S232), the arithmetic unit 220 skips the subsequent processes at Step S233 to Step S235 and performs the process at Step S236 that will be described later.

Furthermore, when the flag value FF is not 1, i.e., when the gaze point P arrives at the specific area A5 for the first time (No at Step S232), the arithmetic unit 220 extracts the measurement result of the timer TT1 as the arrival time data in the target display period (Step S233). Furthermore, the arithmetic unit 220 allows the storage 222 to store the movement frequency data in the target display period that indicates the number of movement of the gaze point P among the areas before the gaze point P arrives at the specific area A5 (Step S234). After that, the arithmetic unit 220 changes the flag value FF to 1 (Step S235).

Then, the arithmetic unit 220 determines whether the area in which the gaze point P is present at the latest detection, i.e., the final area, is the specific area A5 (Step S236). When the arithmetic unit 220 determines that the final area is the specific area A5 (Yes at Step S236), the arithmetic unit 220 skips the subsequent processes at Step S237 and Step S238 and performs the process at Step S239 that will be described later. Furthermore, when it is determined that the final area is not the specific area A5 (No at Step S236), the arithmetic unit 220 increments the integrated number that indicates the number of movement of the gaze point P among the areas by 1 (Step S237), and changes the final area to the specific area A5 (Step S238). Furthermore, the arithmetic unit 220 increments the count value CNTA1 that indicates the presence time data in the target display period in the specific area A5 by 1 (Step S239).

After that, the arithmetic unit 220 performs a determination whether or not the gaze point P is present in the specific feature area A1 (Step S240). When it is determined that the gaze point P is present in the specific feature area A1 (Yes at Step S240), the arithmetic unit 220 increments the count value CNTA1 that indicates the presence time data in the target display period in the specific area A5 by 1 (Step S241). In contrast, when it is determined that the gaze point P is not present in the specific feature area A1 (No at Step S240), the arithmetic unit 220 skips the process at Step S241 and performs the process at Step S230 and the subsequent processes.

Namely, when it is determined that the gaze point P is present in the specific feature area A1, in also at Step S241 in addition to the process at Step S239, the count value CNTA1 that indicates the presence time data in the target display period is incremented by 1. Therefore, when it is determined that the gaze point P is present in the specific feature area A1, the count value CNTA1 that indicates the presence time data in the target display period is totally incremented by 2. In contrast, when it is determined that the gaze point P is present in the specific area A5 but is not present in the specific feature area A1, at Step S239, the count value CNTA1 that indicates the presence time data in the target display period is incremented by 1. However, at Step S241, the count value CNTA1 is not incremented by 1. Therefore, when it is determined that the gaze point P is present in the specific area A5 but is not present in the specific feature area A1, the count value CNTA1 that indicates the presence time data in the target display period is incremented by 1. In this way, different weightings are applied to the presence time data in the target display period between in a case in which it is determined that the gaze point P is present in the specific feature area A1 and in a case in which it is determined that the gaze point P is present in the specific area A5 but is not present in the specific feature area A1.

As described above, the evaluation device 100 according to the present application includes: a display 101S configured to display images; a gaze point detecting unit 214 configured to detect a positional data of a gaze point of a subject who observes the display 101S; a display controller 202 configured to display a task target object that includes a task feature portion and that is to be gazed at by the subject and instruction information that is a task related to the task target object on the display 101S, and to display, after displaying the task target object and the instruction information, a specific target object that includes a specific feature portion corresponding to the task feature portion and that is a correct answer to the instruction information and comparison target objects each of which differs from the specific target object on the display 101S; an area setting unit 216 configured to set a specific feature area A1 for the specific feature portion and comparison areas A2 to A4 for the comparison target objects on the display 101S; a determination unit 218 configured to determine, based on the positional data of the gaze point, whether the gaze point is present in each of the specific feature area A1 and the comparison areas A2 to A4; an arithmetic unit 202 configured to calculate, based on a determination result by the determination unit 218, a gaze point transition data in a target display period; and an evaluating unit 224 configured to obtain, based on the gaze point transition data in the target display period, an evaluation data of the subject.

Furthermore, the evaluation method according to the present application includes: displaying images on a display 101S; detecting a positional data of a gaze point of a subject who observes the display 101S; displaying a task target object that includes a task feature portion and that is to be gazed at by the subject and instruction information that is a task related to the task target object on the display 101S, and displaying, after displaying the task target object and the instruction information, a specific target object that includes a specific feature portion corresponding to the task feature portion and that is a correct answer to the instruction information and comparison target objects each of which differs from the specific target object on the display 101S; setting a specific feature area A1 for the specific feature portion and comparison areas A2 to A4 for the comparison target objects on the display 101S; determining, based on the positional data of the gaze point, whether the gaze point is present in each of the specific feature area A1 and the comparison areas A2 to A4; calculating, based on a determination result, a gaze point transition data in a target display period; and obtaining, based on the gaze point transition data in the target display period, an evaluation data of the subject.

Furthermore, the non-transitory storage medium according to the present application stores the evaluation program that causes a computer to execute: a process of displaying images on a display 101S; a process of detecting a positional data of a gaze point of a subject who observes the display 101S; a process of displaying a task target object that includes a task feature portion and that is to be gazed at by the subject and instruction information that is a task related to the task target object on the display 101S, and displaying, after displaying the task target object and the instruction information, a specific target object that includes a specific feature portion corresponding to the task feature portion and that is a correct answer to the instruction information and comparison target objects each of which differs from the specific target object on the display 101S; a process of setting a specific feature area A1 for the specific feature portion and comparison areas A2 to A4 for the comparison target objects on the display 101S; a process of determining, based on the positional data of the gaze point, whether the gaze point is present in each of the specific feature area A1 and the comparison areas A2 to A4; a process of calculating, based on a determination result, a gaze point transition data in a target display period; and a process of obtaining, based on the gaze point transition data in the target display period, an evaluation data of the subject.

According to the embodiments, by setting the specific feature area for the specific feature portion in the target display operation, it is possible to evaluate whether the subject makes a determination by gazing at the specific feature portion of the specific target object. Therefore, it is possible to prevent a case in which the gaze point P of the subject is accidentally directed to the specific target object from being determined as a correct answer. Accordingly, it is possible to perform evaluation of the subject with high accuracy.

Furthermore, in the evaluation device 100 according to the embodiment, each of the task feature portion and the specific feature portion is a recess portion or a protruding portion of a pattern that constitutes each of the task target object and the specific target object or a connection portion of the multiple patterns. Since the subject is able to easily gaze the task feature portion and the specific feature portion, it is possible to prevent a case in which the gaze point of the subject is accidentally directed to the specific target object from being determined as a correct answer.

Furthermore, in the evaluation device 100 according to the embodiments, the area setting unit 216 sets the task feature area A for the task feature portion and the instruction area B for the instruction information on the display. The determination unit 218 determines, based on the positional data of the gaze point, whether the gaze point P is present in each of the task feature area A and the instruction area B, and the arithmetic unit 220 calculates, based on the determination result by the determination unit 218, the gaze point transition data in the instruction display period that indicates the transition of the gaze point P. Accordingly, it is possible to evaluate the subject from a viewpoint whether, after the subject viewed the instruction information displayed on the display 101S, the subject attempts to gaze at the task feature area A of the task target object indicated by the instruction information.

Furthermore, in the evaluation device 100 according to the embodiments, the area setting unit 216 further sets, on the display 101S, the specific area A5 for the specific portion. The determination unit 218 determines, based on the positional data of the gaze point P, whether the gaze point P is present in each of the specific feature area A1, the specific area A5, and the comparison areas A2 to A4, and the evaluating unit 220 obtains the evaluation data by applying different weightings to a case in which the gaze point P is present in the specific feature area A1 and to a case in which the gaze point P is not present in the specific feature area A1 but is present in the specific area A5. Therefore, it is possible to distinguish a case in which the subject gazes at the specific feature portion from a case in which the subject gazes at the specific target object that is other than the specific feature portion. Accordingly, it is possible to perform evaluation of the subject with high accuracy.

The technical scope of the present embodiments is not limited to the embodiments described above and various modifications are possible as long as they do not depart from the spirit of the present embodiments. For example, in the embodiments described above, a case has been described as one example in which the area setting unit 216 sets the specific feature area A1 by using the recess portion or the protruding portion of the pattern that constitutes the specific target object or by using the connection portion of the multiple patterns as the specific feature portion. However, the embodiments are not limited thereto. For example, it may also be possible to set an area for the portion of the task target object gazed at by the subject in the instruction display operation as the specific feature area A1.

In this case, in the instruction display operation, the gaze point detecting unit 214 detects the area that has been gazed at by the subject. At this time, the gaze point detecting unit 214 obtains a positional relationship between coordinates of the portion in which the task target object is displayed on the display 101S and coordinates of the area that has been gazed at by the subject. After that, in the target display operation, the area setting unit 216 sets the specific feature area A1 in an area corresponding to the area detected by the gaze point detecting unit 214 among areas included in the specific target object displayed on the display 101S. In this case, the area setting unit 216 sets the specific feature area A1 at a position corresponding to the coordinates of the portion in which the specific target object is displayed on the display 101S based on a relative positional relationship between the coordinates of the portion in which the task target object is displayed on the display 101S and the coordinates of the area that is gazed at by the subject.

Figure 20:
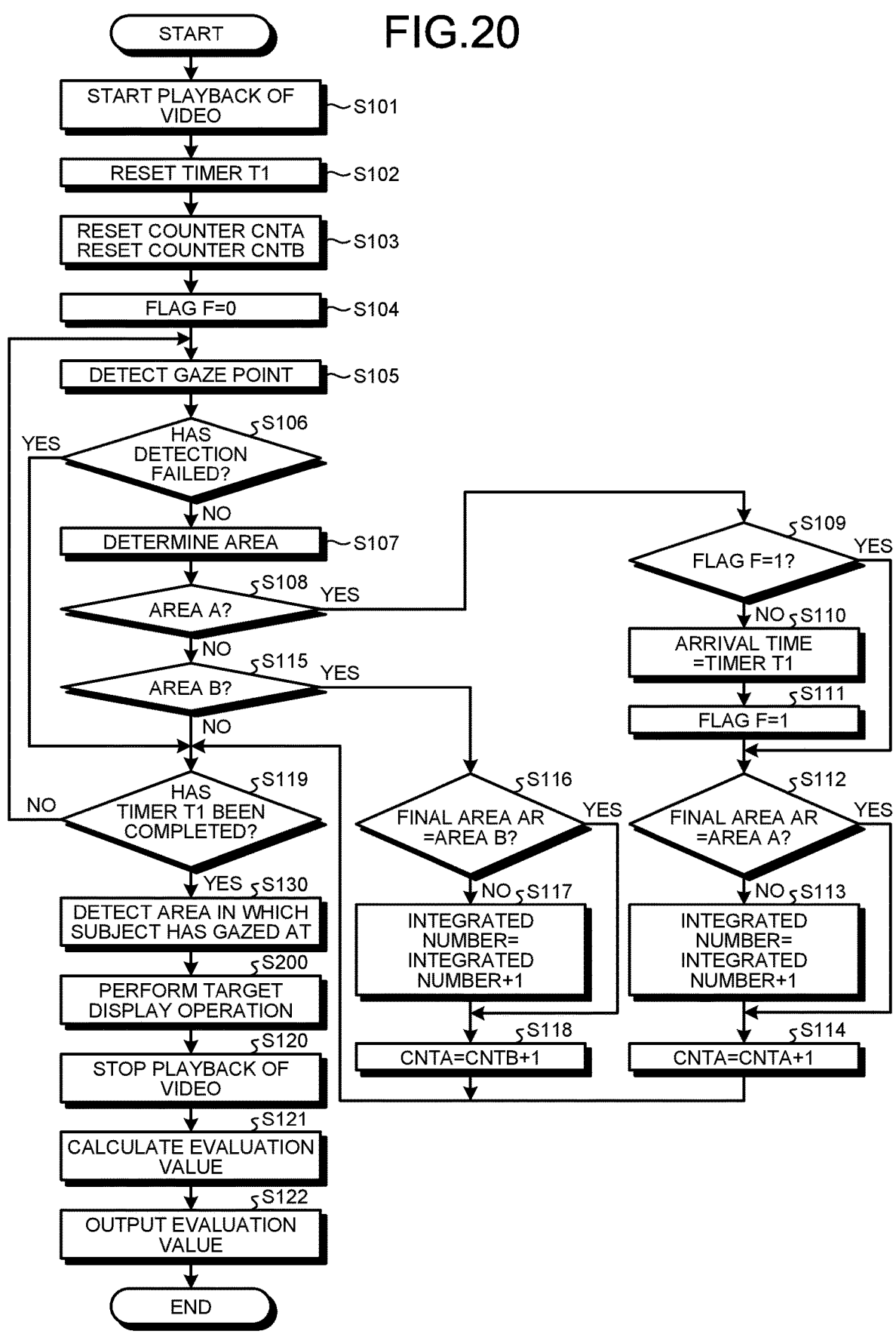
FIG. 20 is a flowchart illustrating another example of the evaluation method in the instruction display operation.
Figure 21:
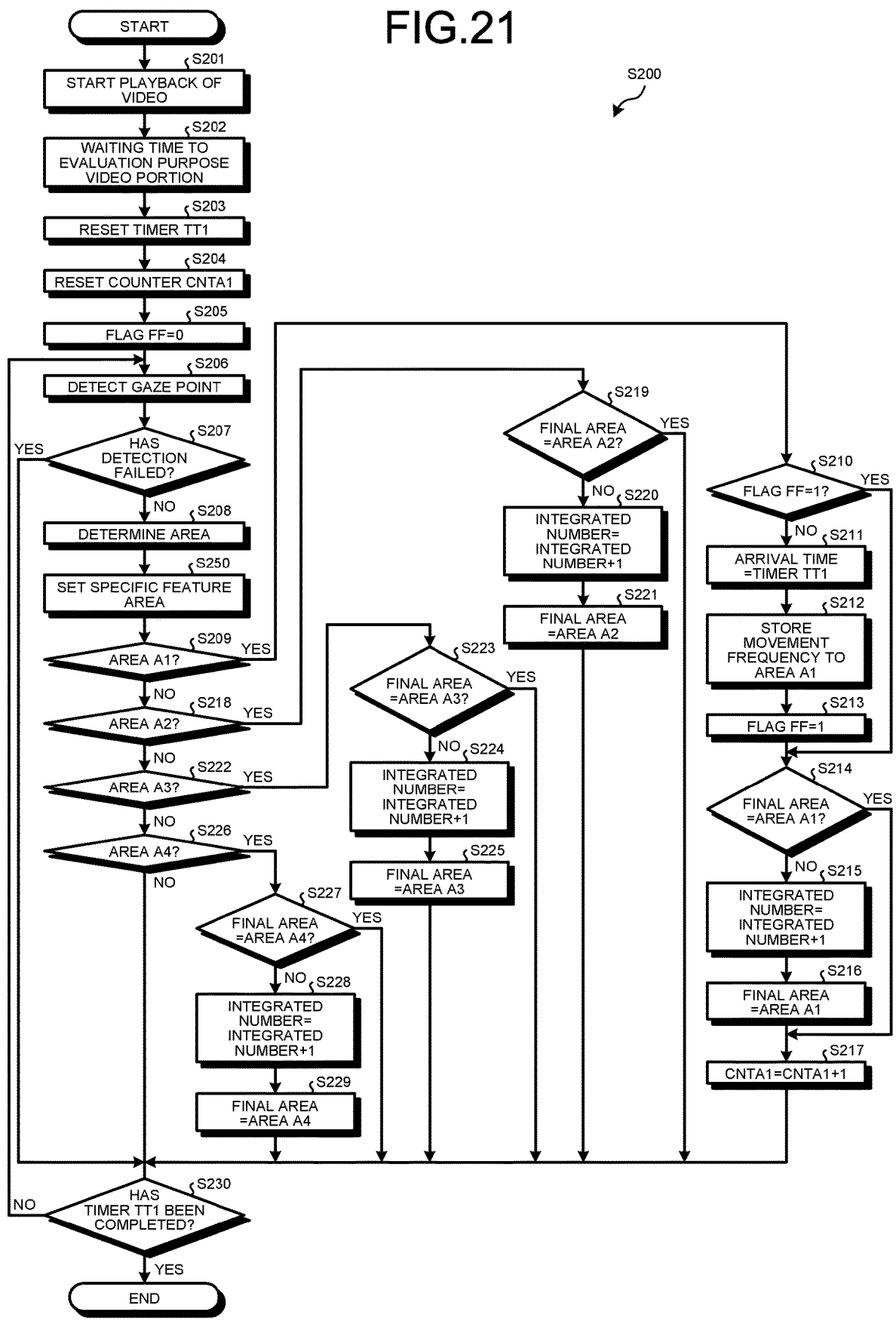
FIG. 21 is a flowchart illustrating another example of the evaluation method in the target display operation.

In the following, an example of the evaluation method in this case will be described. FIG. 20 and FIG. 21 are flowcharts each illustrating the evaluation method according to the modification. FIG. 20 mainly illustrates an example of the instruction display operation, whereas FIG. 21 illustrates an example of the target display operation.

As illustrated in FIG. 20, in the instruction display operation, the processes form Step S101 to Step S119 are performed in a similar manner to those performed in the embodiments described above. At Step S119, when it is determined, by the arithmetic unit 220, that the time reaches the completion time of the playback of the video (Yes at Step S119), the gaze point detecting unit 214 detects the area that is gazed at by the subject and obtains the positional relationship between the coordinates of the detected area and the coordinates of the portion in which the task target object is displayed (Step S130). After that, the target display operation is performed (Step S200).

As illustrated in FIG. 21, in the target display operation, the processes from Step S201 to Step S208 are performed in a similar manner to those performed in the embodiments described above. After the process at Step S208 has been performed, the area setting unit 216 sets the specific feature area A1 in an area corresponding to the area detected by the gaze point detecting unit 214 among areas included in the specific target object displayed on the display 101S (Step S250). After that, the process at Step S209 and the subsequent processes are performed based on the set specific feature area A1. In this case, the content of the process at Step S209 and the subsequent processes is the same as that described in the embodiments above.

In this way, by using the area corresponding to the area gazed at by the subject in the task target object as the specific feature area, it is possible to evaluate the subject with higher accuracy from a viewpoint whether or not the subject gazes at and memorizes the task feature area of the task target object, and whether or not the subject gazes at and determines the specific feature area of the specific target object.

It is possible to use the evaluation device, the evaluation method, and the evaluation program according to the embodiment in, for example, a line-of-sight detecting device.

According to an aspect of the present application, it is possible to provide an evaluation device, an evaluation method, and an evaluation program capable of evaluating cognitive functional impairment and brain functional impairment with high accuracy.

Although the application has been described with respect to specific embodiments for a complete and clear application, the appended claims are not to be thus limited but are to be construed as embodying all modifications and alternative constructions that may occur to one skilled in the art that fairly fall within the basic teaching herein set forth.

What is claimed is:

1. An evaluation device comprising:
a display configured to display images;
a gaze point detecting unit configured to detect a positional data of a gaze point of a subject who observes the display;
a display controller configured to display a task target object that includes a task feature portion and that is to be gazed at by the subject and instruction information that is a task related to the task target object on the display, and to display, after displaying the task target object and the instruction information, a specific target object that includes a specific feature portion corresponding to the task feature portion and that is a correct answer to the instruction information and comparison target objects each of which differs from the specific target object on the display;
an area setting unit configured to set a specific area for an entirety of the specific target object, a specific feature area for the specific feature portion which is part of the specific target object, and comparison areas for the comparison target objects on the display;
a determination unit configured to determine, based on the positional data of the gaze point, whether the gaze point is present in each of the specific feature area and the comparison areas;
an arithmetic unit configured to calculate, based on a determination result by the determination unit, a gaze point transition data in a target display period; and
an evaluating unit configured to obtain, based on the gaze point transition data in the target display period, an evaluation data of the subject by applying different weightings to a case in which the gaze point is present in the specific feature area and to a case in which the gaze point is not present in the specific feature area but is present in the specific area.

2. The evaluation device according to claim 1, wherein each of the task feature portion and the specific feature portion corresponds to a recess portion or a protruding portion of a pattern that constitutes each of the task target object and the specific target object, or a connection portion of multiple patterns.

3. The evaluation device according to claim 1, wherein the area setting unit is further configured to set a task feature area for the task feature portion and an instruction area for the instruction information on the display, the determination unit is further configured to determine, based on the positional data of the gaze point, whether the gaze point is present in each of the task feature area and the instruction area, and
the arithmetic unit is further configured to calculate, based on the determination result by the determination unit, the gaze point transition data in an instruction display period.

4. An evaluation method comprising:
displaying images on a display;
detecting a positional data of a gaze point of a subject who observes the display;
displaying a task target object that includes a task feature portion and that is to be gazed at by the subject and instruction information that is a task related to the task target object on the display, and displaying, after displaying the task target object and the instruction information, a specific target object that includes a specific feature portion corresponding to the task feature portion and that is a correct answer to the instruction information and comparison target objects each of which differs from the specific target object on the display;
setting a specific area for an entirety of the specific target object, a specific feature area for the specific feature portion which is part of the specific target object, and comparison areas for the comparison target objects on the display;
determining, based on the positional data of the gaze point, whether the gaze point is present in each of the specific feature area and the comparison areas;
calculating, based on a determination result, a gaze point transition data in a target display period; and
obtaining, based on the gaze point transition data in the target display period, an evaluation data of the subject by applying different weightings to a case in which the gaze point is present in the specific feature area and to a case in which the gaze point is not present in the specific feature area but is present in the specific area.

5. A non-transitory storage medium that stores an evaluation program that causes a computer to execute:
a process of displaying images on a display;
a process of detecting a positional data of a gaze point of a subject who observes the display;
a process of displaying a task target object that includes a task feature portion and that is to be gazed at by the subject and instruction information that is a task related to the task target object on the display, and displaying, after displaying the task target object and the instruction information, a specific target object that includes a specific feature portion corresponding to the task feature portion and that is a correct answer to the instruction information and comparison target objects each of which differs from the specific target object on the display;
a process of setting a specific area for an entirety of the specific target object, a specific feature area for the specific feature portion which is part of the specific target object, and comparison areas for the comparison target objects on the display;
a process of determining, based on the positional data of the gaze point, whether the gaze point is present in each of the specific feature area and the comparison areas;
a process of calculating, based on a determination result, a gaze point transition data in a target display period; and a process of obtaining, based on the gaze point transition data in the target display period, an evaluation data of the subject by applying different weightings to a case in which the gaze point is present in the specific feature area and to a case in which the gaze point is not present in the specific feature area but is present in the specific area.

* * * * *